United States Patent
Chi et al.

(10) Patent No.: US 9,865,824 B2
(45) Date of Patent: Jan. 9, 2018

(54) ORGANOMETALLIC COMPOUND, ORGANIC LIGHT-EMITTING DEVICE, AND LIGHTING DEVICE EMPLOYING THE SAME

(71) Applicants: INDUSTRIAL TECHNOLOGY RESEARCH INSTITUTE, Hsinchu (TW); National Tsing Hua University, Hsinchu (TW)

(72) Inventors: Yun Chi, Hsinchu (TW); Yu-Shan Tsai, Tainan (TW); Jia-Ling Liao, Xihu Township (TW); Mei-Rurng Tseng, Hsinchu (TW); Jin-Sheng Lin, Taipei (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 867 days.

(21) Appl. No.: 14/141,020

(22) Filed: Dec. 26, 2013

(65) Prior Publication Data

US 2015/0123082 A1    May 7, 2015

(30) Foreign Application Priority Data

Nov. 7, 2013    (TW) .............................. 102140424 A

(51) Int. Cl.
*H01L 51/00*    (2006.01)
*C07F 15/00*    (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS

| | | |
|---|---|---|
| 2002/0134984 A1 | 9/2002 | Igarashi |
| 2002/0182441 A1 | 12/2002 | Lamansky et al. |

(Continued)

FOREIGN PATENT DOCUMENTS

| | | |
|---|---|---|
| JP | 2006-182921 A | 7/2006 |
| JP | 2008-74831 A | 4/2008 |

(Continued)

OTHER PUBLICATIONS

Chang et al., "A New Class of Sky-Blue-Emitting Ir(III) Phosphors Assembled Using Fluorine-Free Pyridyl Pyrimidine Cyclometalates: Application toward High-Performance Sky-Blue— and White-Emitting OLEDs," Jul. 17, 2013, ACS Appl. Mater Interfaces 5, pp. 7341-7351.*

(Continued)

*Primary Examiner* — Robert A Vetere
(74) *Attorney, Agent, or Firm* — Birch, Stewart, Kolasch & Birch, LLP

(57) ABSTRACT

Organometallic compounds, organic light-emitting devices, and lighting devices employing the same are provided. The organometallic compound has a chemical structure represented by formula (I) or (II):

(Continued)

(56) References Cited

U.S. PATENT DOCUMENTS

| | | |
|---|---|---|
| 2003/0072964 A1 | 4/2003 | Kwong et al. |
| 2005/0156173 A1* | 7/2005 | Yamazaki ........... H01L 27/3244 257/72 |
| 2008/0217605 A1* | 9/2008 | Wallace ............... C08G 61/122 257/40 |
| 2011/0187265 A1 | 8/2011 | De Cola et al. |
| 2012/0169213 A1 | 7/2012 | De Cola et al. |
| 2012/0181511 A1 | 7/2012 | Ma et al. |
| 2013/0004986 A1 | 1/2013 | De Cola et al. |
| 2013/0026452 A1 | 1/2013 | Kottas et al. |
| 2013/0281693 A1 | 10/2013 | Inoue et al. |

FOREIGN PATENT DOCUMENTS

| | | | |
|---|---|---|---|
| JP | 2008074831 A | * | 4/2008 |
| TW | 200720399 A | | 6/2007 |
| TW | 201132737 A | | 10/2011 |
| WO | WO 2005/123873 A1 | | 12/2005 |
| WO | WO 2006/008976 A1 | | 1/2006 |
| WO | WO 2009/107497 A1 | | 9/2009 |
| WO | WO 2012/005172 A1 | | 1/2012 |

OTHER PUBLICATIONS

JP 2008-074831, machine translation, 2008.*
Taiwanese Office Action dated Dec. 4, 2014 for corresponding Taiwanese application No. 103101570.
Chih-Hao et al., "A New Class of Sky-Blue-Emitting Ir(III) Phosphors Assembled Using Fluorine-Free Pyridyl Pyrimidine Cyclometalates: Application toward High-Performance Sky-Blue— and White-Emitting OLEDs", ACS Applied Materials & Interfaces, vol. 5, 2013, pp. 7341-7351.
Jeon et al., "External Quantum Efficiency Above 20% in Deep Blue Phosphorescent Organic Light-Emitting Diodes," Advanced Materials, vol. 23, 2011, pp. 1436-1441.
Park et al., "Fused indole derivatives as high triplet energy hole transport materials for deep blue phosphorescent organic light-emitting diodes," Journal of Materials Chemistry, vol. 22, 2012, pp. 3099-3104.
Yang et al., "Blue-Emitting Heteroleptic Indium(III) Complexes Suitable for High-Efficiency Phosphorescent OLEDs," Angewandte Chemie International Edition, vol. 119, 2007, pp. 2470-2473.
Yang et al., "Deep-Blue-Emitting Heteroleptic Iridium(III) Complexes Suited for Highly Effcient Phosphorescent OLEDs," Chemistry of Materials, vol. 24, 2012, pp. 3684-3695.
Zhu et al., "Highly Efficient Green and Blue-Green Phosphorescent OLEDs Based on Iridium Complexes with the Tetraphenylimidodiphosphinate Ligand," Advanced Materials, vol. 23, 2011, pp. 4041-4046.

* cited by examiner

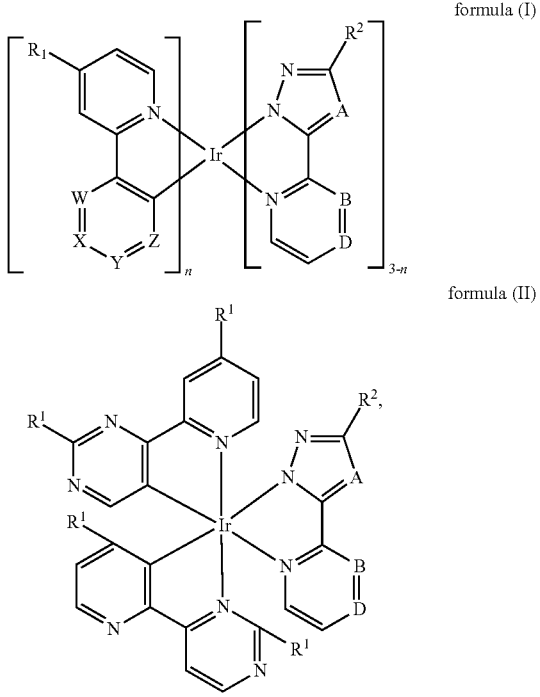

formula (I)

formula (II)

wherein n is 1 or 2; each $R^1$ is independent and can be hydrogen, $C_{1-8}$ alkyl, $C_{1-8}$ alkoxy, $C_{5-10}$ aryl, or $C_{2-8}$ heteroaryl; each $R^2$ is independent and can be hydrogen, $C_{1-8}$ fluoroalkyl, or $C_{1-8}$ alkyl; A is N, or CH; B is N, or CH; D is N, or C—$R^3$, wherein $R^3$ is H, or $C_{1-8}$ alkyl; and $R^1$ is not hydrogen when $R^2$ is hydrogen.

20 Claims, 5 Drawing Sheets

(51) Int. Cl.
    *C09K 11/06*     (2006.01)
    *H01L 51/50*     (2006.01)
(52) U.S. Cl.
    CPC .... *C09K 2211/185* (2013.01); *H01L 51/5012* (2013.01); *H01L 51/5016* (2013.01)

ORGANOMETALLIC COMPOUND, ORGANIC LIGHT-EMITTING DEVICE, AND LIGHTING DEVICE EMPLOYING THE SAME

CROSS REFERENCE TO RELATED APPLICATIONS

This application is based upon and claims the benefit of priority from the prior Taiwan Patent Application No. 102140424, filed on 7 Nov. 2013, the entire contents of which are incorporated herein by reference.

TECHNICAL FIELD

The disclosure relates to an organometallic compound, organic light-emitting device, and lighting device employing the same.

BACKGROUND

An organic light-emitting diode (OLED) is a light-emitting diode employing an organic electroluminescent layer as an active layer. OLED display devices have high luminescent efficiency and long operating lifespans. In comparison with liquid-crystal displays, due to the characteristic of spontaneous emission, a device employing an organic light-emitting diode is free of a back-light source.

Generally, an organic light-emitting device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

SUMMARY

According to an embodiment of the disclosure, the disclosure provides an organometallic compound having a Formula (I) or Formula (II):

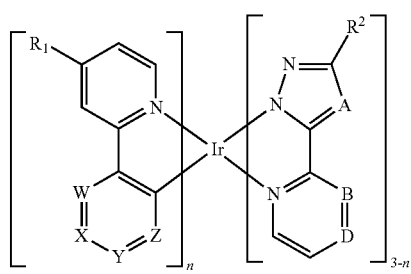

Formula (I)

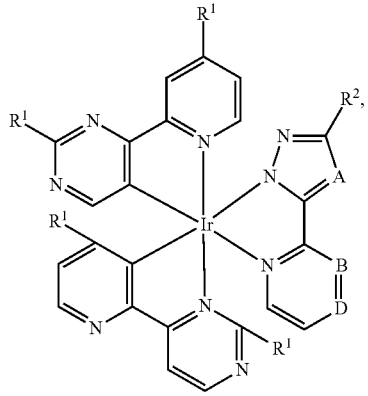

Formula (II)

wherein n is 1 or 2; each $R^1$ is independent and can be hydrogen, $C_{1-8}$ alkyl, $C_{1-8}$ alkoxy, $C_{5-10}$ aryl, or $C_{2-8}$ heteroaryl; each $R^2$ is independent and can be hydrogen, $C_{1-8}$ fluoroalkyl, or $C_{1-8}$ alkyl; A is N, or CH; B is N, or CH; D is N, or C—$R^3$, wherein $R^3$ is H, or $C_{1-8}$ alkyl; and $R^1$ is not hydrogen when $R^2$ is hydrogen. Particularly, one of following two conditions (1) and (2) is met: (1) X and Z are N, W is CH, and Y is C—$R^4$, wherein $R^4$ is hydrogen, $C_{1-8}$ alkyl, $C_{1-8}$ alkoxy, $C_{5-10}$ aryl, or $C_{2-8}$ heteroaryl; and (2) W and Y are N, Z is CH, and X is C—$R^4$, wherein $R^4$ is hydrogen, $C_{1-8}$ alkyl, $C_{1-8}$ alkoxy, $C_{5-10}$ aryl, or $C_{2-8}$ heteroaryl.

According to another embodiment of the disclosure, the disclosure provides an organic light-emitting device, wherein the device includes a pair of electrodes; and an electroluminescent element disposed between the pair of electrodes. In particular, the electroluminescent element includes the aforementioned organometallic compound.

According to other embodiments of the disclosure, the disclosure also provides a lighting device including: a lead frame; and the aforementioned organic light-emitting device disposed on the lead frame.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
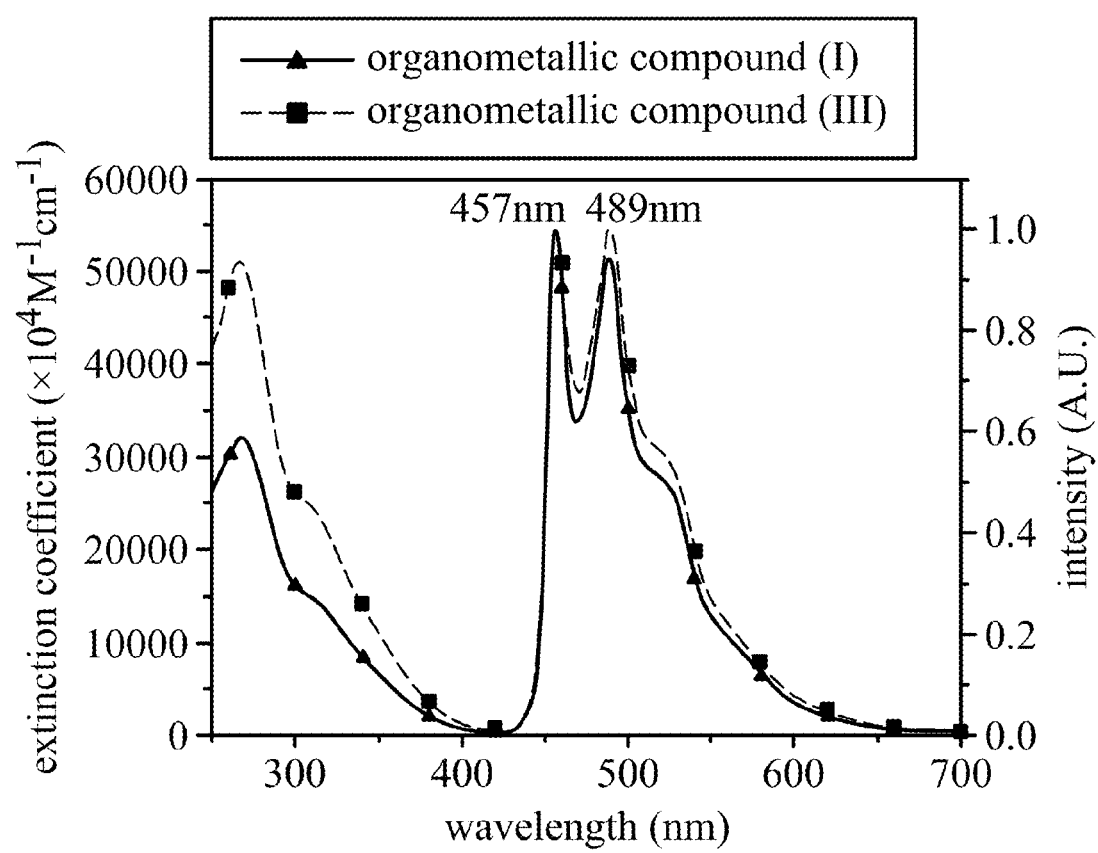
FIG. 1 shows ultraviolet absorption spectra and photoluminescence excitation spectra of the organometallic compounds (I) and (III) of the disclosure.

The following description is of the best-contemplated mode of carrying out the disclosure. This description is made for the purpose of illustrating the general principles of the disclosure and should not be taken in a limiting sense. The scope of the disclosure is best determined by reference to the appended claims.

Organic Compound

According to embodiments of the disclosure, the disclosure provides an organometallic compound, which has a pyrimidine-containing ligand and a pyrazole-containing ligand bonded with Ir, that can serve as a phosphorescent light-emitting material. Since the organometallic compounds of the disclosure have a suitable highest occupied molecular orbital (HOMO) energy gap (between about 5.6 eV and 5.95 eV) and a lowest unoccupied molecular orbital (LUMO) energy gap (between about 2.9 ev and 3.1 eV), the organometallic compounds of the disclosure can serve as electroluminescent material (such as a phosphorescent dopant used in the light-emitting layer) for increasing the luminous efficiency of the organic light-emitting device. In comparison with a conventional blue phosphorescence light-emitting material FIrpic (having a structure of

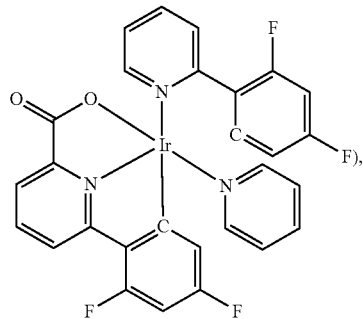

the organometallic compounds of the disclosure have a superior thermal stability. Therefore, the organometallic compounds of the disclosure can be substituted for the conventional blue phosphorescence light-emitting material FIrpic, in order to increase the lifetime of the organic light-emitting device.

According to embodiments of the disclosure, the disclosure discloses an organometallic compound that has a Formula (I):

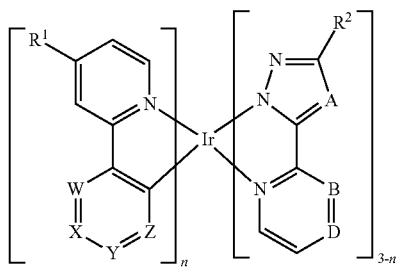

Formula (I)

wherein, n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; A is N, or CH; B is N, or CH; D is N, or C—$R^3$, wherein $R^3$ is hydrogen, or $C_{1-8}$ alkyl, wherein $R^1$ is not hydrogen when $R^2$ is hydrogen. Furthermore, one of following two conditions (1) and (2) is met: (1) X and Z are N, W is CH, and Y is C—$R^4$, wherein $R^4$ is hydrogen, $C_{1-8}$ alkyl, $C_{1-8}$ alkoxy, $C_{5-10}$ aryl, or $C_{2-8}$ heteroaryl; and (2) W and Y are N, Z is CH, and X is C—$R^4$, wherein $R^4$ is hydrogen, $C_{1-8}$ alkyl, $C_{1-8}$ alkoxy, $C_{5-10}$ aryl, or $C_{2-8}$ heteroaryl.

According to embodiments of the disclosure, the disclosure discloses an organometallic compound that has a Formula (II):

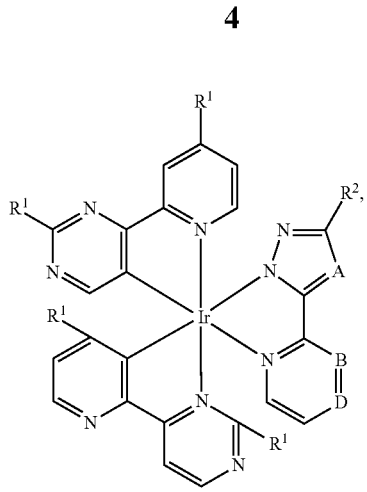

Formula (II)

wherein n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group, wherein $R^1$ is not hydrogen when $R^2$ is hydrogen; A is N, or CH; B is N, or CH; D is N, or C—$R^3$, wherein $R^3$ is hydrogen, or $C_{1-8}$ alkyl.

According to embodiments of the disclosure, each $R^1$ is independently hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

Each $R^2$ is independently methyl group, ethyl group, propyl group, isopropyl group, butyl group, tert-butyl group, pentyl group, hexyl group, fluoromethyl group, fluoroethyl group, or fluoropropyl group.

Each $R^3$ is independently methyl group, ethyl group, propyl group, isopropyl group, butyl group, tert-butyl group, pentyl group, or hexyl group.

Each $R^4$ is independently hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

According to other embodiments of the disclosure, the organometallic compound having Formula (I) can be

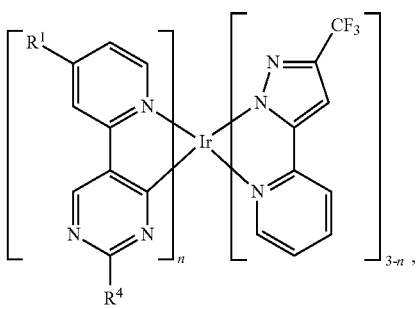

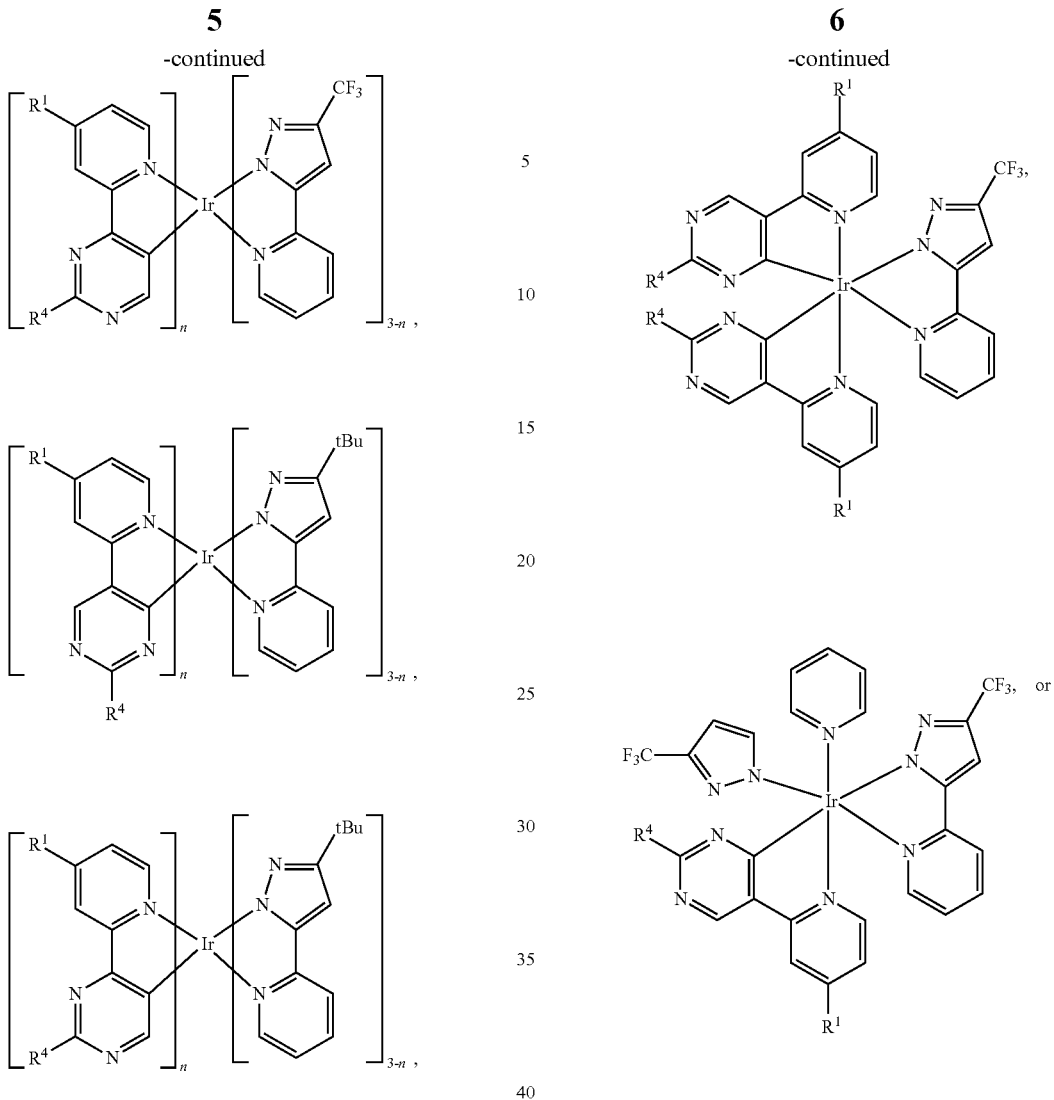

wherein each $R^1$ is independently hydrogen, $C_{1-8}$ alkyl, $C_{1-8}$ alkoxy, $C_{5-10}$ aryl, or $C_{2-8}$ heteroaryl; each $R^4$ is independently hydrogen, $C_{1-8}$ alkyl, $C_{1-8}$ alkoxy, $C_{5-10}$ aryl, or $C_{2-8}$ heteroaryl; and $R^1$ is not hydrogen when $R^4$ is hydrogen.

According to other embodiments of the disclosure, the organometallic compound having Formula (I) can be

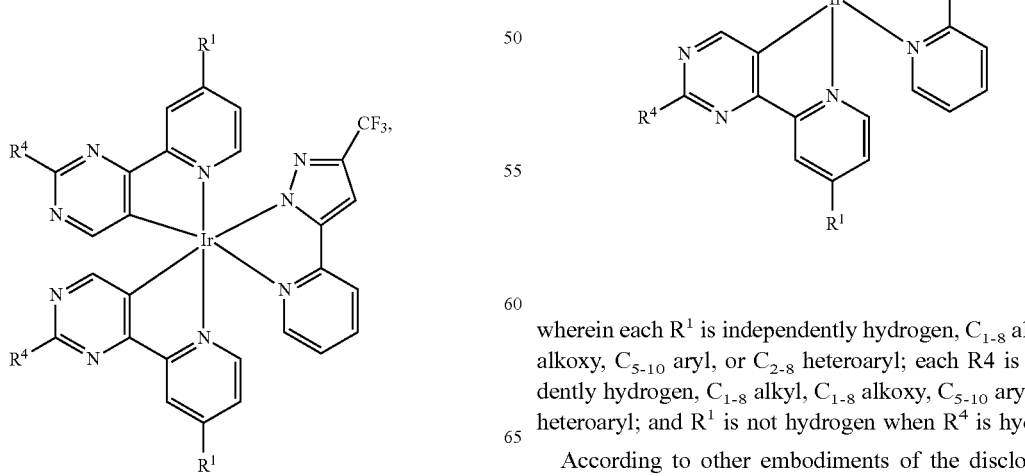

wherein each $R^1$ is independently hydrogen, $C_{1-8}$ alkyl, $C_{1-8}$ alkoxy, $C_{5-10}$ aryl, or $C_{2-8}$ heteroaryl; each R4 is independently hydrogen, $C_{1-8}$ alkyl, $C_{1-8}$ alkoxy, $C_{5-10}$ aryl, or $C_{2-8}$ heteroaryl; and $R^1$ is not hydrogen when $R^4$ is hydrogen.

According to other embodiments of the disclosure, the organometallic compound having Formula (I) can be

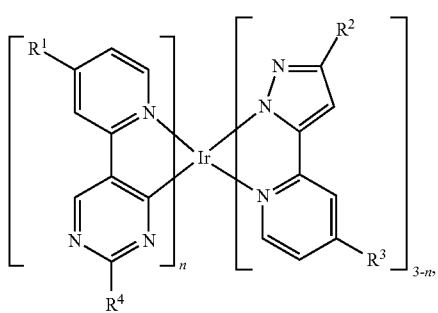

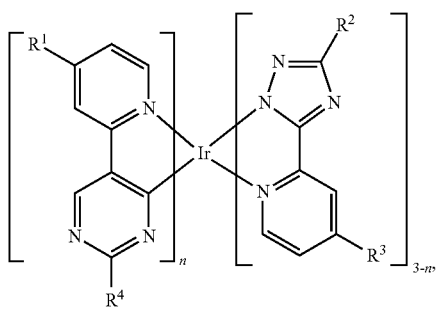

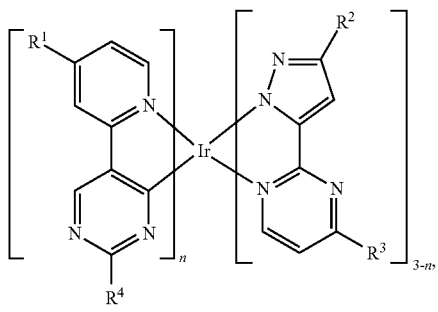

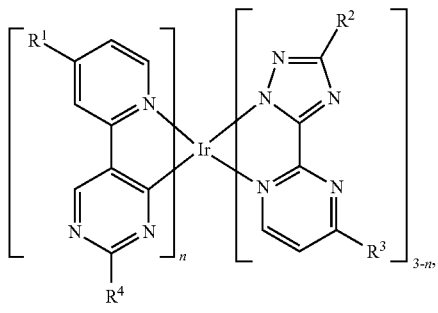

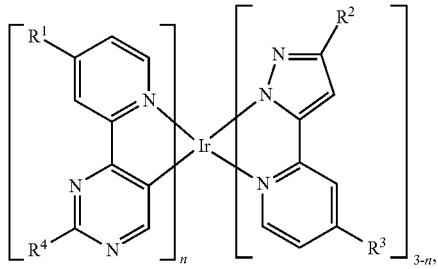

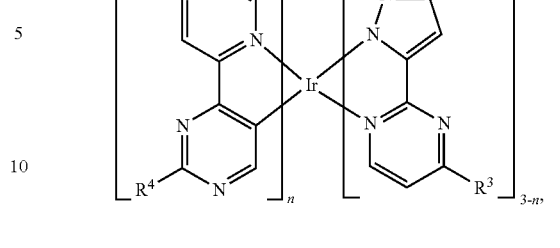

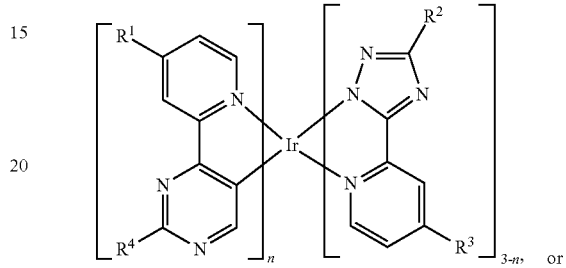

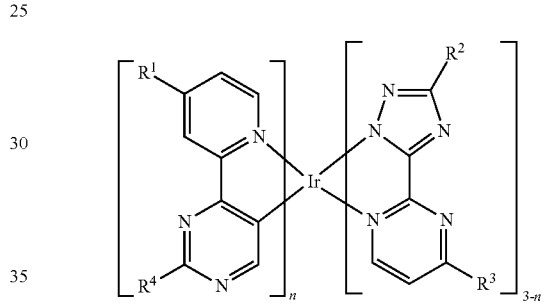

wherein, each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; each $R^3$ is independently hydrogen, or $C_{1-8}$ alkyl; and, each $R^4$ is independently hydrogen, $C_{1-8}$ alkyl, $C_{1-8}$ fluoroalkyl, $C_{1-8}$ alkoxy, $C_{5-10}$ aryl, or $C_{2-8}$ heteroaryl. In particular, $R^1$, $R^2$, $R^3$, and $R^4$ are not hydrogen at the same time.

The following examples are intended to illustrate the disclosure more fully without limiting the scope, since numerous modifications and variations will be apparent to those skilled in this art.

Example 1: Preparation of Organometallic Compound (I)

2 g (14.63 mmol) of compound (1) (2,2,2-trimethylacetamidine hydrochloride), and 4.85 mL (29.27 mmol) of compound (2) (1,1,3,3-tetramethoxypropane) were added into a reaction bottle. Next, the reaction bottle was disposed into a high-pressure autoclave, and heated at 200° C. for 2.5 hr. After cooling, the result was washed by dichloromethane-methanol co-solvent (with a small amount of triethylamine). After concentrating and purification by column chromatography, a compound (3) (2-t-Butyl-pyrimidine) was obtained with a yield of 71%. The synthesis pathway of the above reaction was as follows:

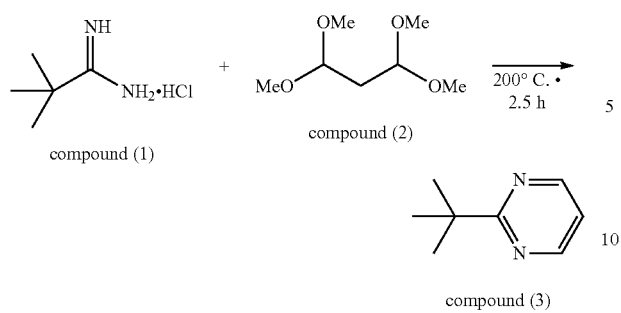

compound (1) + compound (2) →(200° C. 2.5 h)→ compound (3)

The physical measurement of the compound (3) is listed below: $^1$H NMR (400 MHz, CDCl$_3$, 294 K): δ 8.66 (d, J$_{HH}$=4.8 Hz, 2H), 7.06 (t, J$_{HH}$=4.8 Hz, 1H), 1.39 (s, 9H)

Next, 0.23 g (1.68 mmol) of compound (3), 10 ml of glacial acetic acid, and 0.21 g (2.53 mmol) of CH$_3$COONa were added into a reaction bottle. After heating to 80° C., 0.1 mL (1.86 mmol) of Br$_2$ was added into the reaction bottle dropwisely, and then heated at 80° C. for 3 hr. After cooling to room temperature, water was added into the reaction bottle to dilute the mixture, and then NaOH was added into the reaction bottle to adjust the pH value to 7.0. Next, the result was extracted three times by dichloromethane as the extraction solvent. Next, an organic phase was separated and dried by Na$_2$SO$_4$, obtaining compound (4) (2-t-Butyl-5-bromopyrimidine). The synthesis pathway of the above reaction was as follows:

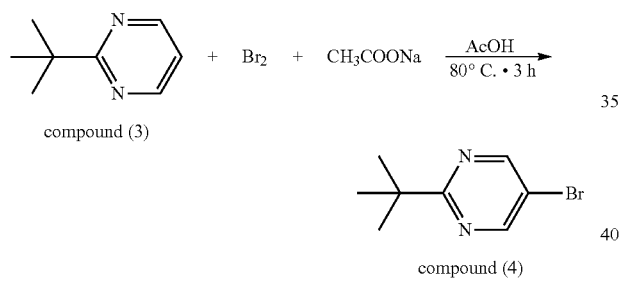

The physical measurement of the compound (4) is listed below:
$^1$H NMR (400 MHz, CDCl$_3$, 294 K): δ 8.69 (s, 2H), 1.37 (s, 9H)

Next, 0.3 g of compound (4) (1.39 mmol), 0.72 g of compound (5) (2-(tributylstannyl)pyridine) (1.95 mmol)), 0.11 g of Pd(PPh$_3$)$_4$ 0.09 mmol), and 25 ml of toluene were added into a reaction bottle, and then the mixture was heated to reflux for 24 hr. After cooling to room temperature, 50 m of dichloromethane was added into the reaction bottle. Next, an organic phase was separated after extracting, and then the result was washed by aqueous ammonia (15%, 100 mL) and dried by Na$_2$SO$_4$. After concentrating and purification by column chromatography, compound (6) (2-tert-butyl-5-(pyridin-2-yl)pyrimidine) was obtained with a yield of 92%. The synthesis pathway of the above reaction was as follows:

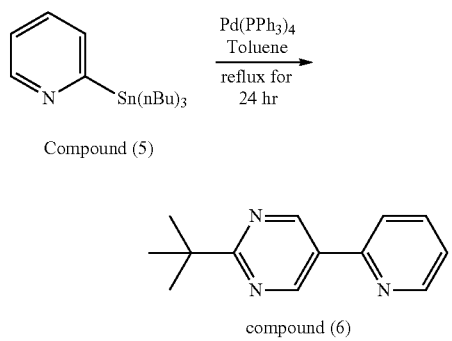

The physical measurement of the compound (6) is listed below: $^1$H NMR (400 MHz, CDCl$_3$, 294 K): δ 9.23 (s, 2H), 8.71 (d, J$_{HH}$=4.8 Hz, 1H), 7.79 (td, J$_{HH}$=8.0, 2.0 Hz, 1H), 7.69 (d, J$_{HH}$=7.6 Hz, 1H), 7.29 (dd, J$_{HH}$=7.6, 4.6 Hz, 1H), 1.41 (s, 9H). Electron Impact-Mass Spectrophotometer (EI-MS): m/z: 213 [M]$^+$ Next, 100 mg of compound (6) (0.28 mmol), 100 mg of IrCl$_3$.3H$_2$O (0.28 mmol), and 20 mL of 2-methoxyethanol were added into a reaction bottle, and then the mixture was heated to reflux for 12 hr under a nitrogen atmosphere. After cooling to room temperature, 0.15 g of 2-(3-(trifluoromethyl)-1H-1,2,4-triazol-5-yl)pyrimidine (fppzH, with a structure of

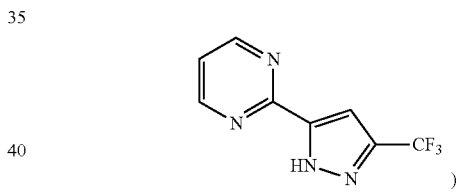

)

(1.42 mmole) and 0.09 g of sodium carbonate (4.26 mmole) were added into a reaction bottle, and then were heated to reflux for 4 hr. After cooling to room temperature, the solvent in the reaction bottle was removed, and then 20 ml of ethyl acetate was added into the reaction bottle. After washing by water, an organic phase was separated and dried by Na$_2$SO$_4$. After purification by column chromatography with ethyl acetate/hexane (1:1) as the extraction solvent and recrystallization, organometallic compound (I) was obtained. The synthesis pathway of the above reaction was as follows:

IrCl$_3$·3H$_2$O +

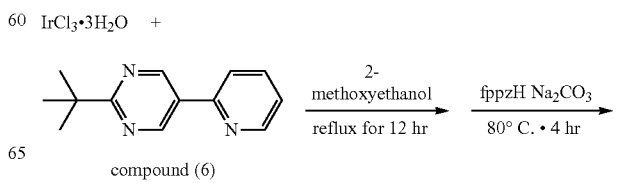

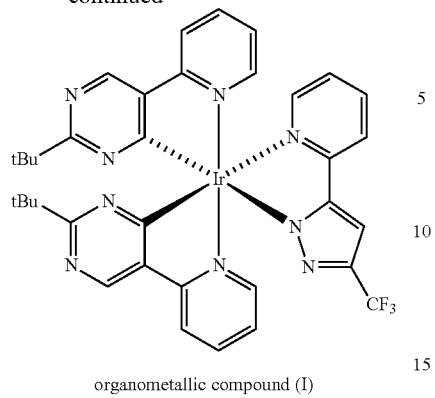

organometallic compound (I)

The physical measurement of the organometallic compound (I) is listed below: $^1$H NMR (400 MHz, CDCl$_3$, 294 K): δ 8.43 (s, 1H), 8.40 (s, 1H), 7.78~7.65 (m, 9H), 7.08~7.01 (m, 2H), 6.96 (t, $J_{HH}$=6.8 Hz, 2H), 1.09 (s, 9H), 1.05 (s, 9H); $^{19}$F-{$^1$H} NMR (376 MHz, CDCl$_3$, 294K): δ −60.11 (s, 3F); MS (FAB, 193Ir). Electron Impact-Mass Spectrophotometer (EI-MS): 831 [M$^{+2}$]$^+$. Elemental analysis: C$_{35}$H$_{33}$F$_3$IrN$_9$: N, 15.21; C, 50.71; H, 4.01. Found: N, 14.75; C, 49.06; H, 4.35.

Example 2: Preparation of Organometallic Compounds (II) and (III)

0.3 g of compound (4) (1.4 mmol), 0.83 g of compound (7) (4-tert-butyl-2-Tributylstannylpyridine) (2.0 mmol), 0.11 g of Pd(PPh$_3$)$_4$ (0.09 mmol), and 25 ml of toluene were added into a reaction bottle, and then the mixture was heated to reflux for 24 hr. After cooling to room temperature, 50 ml of dichloromethane was added into the reaction bottle. Next, an organic phase was separated after extracting, the result was washed with an aqueous ammonia (15%, 100 mL) and dried by Na$_2$SO$_4$. After concentrating and purification by column chromatography, compound (8) (2-tert-butyl-5-(4-tert-butylpyridin-2-yl)pyrimidine) was obtained with a yield of 80%. The synthesis pathway of the above reaction was as follows:

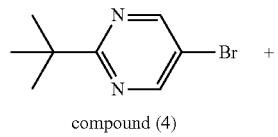

compound (4)

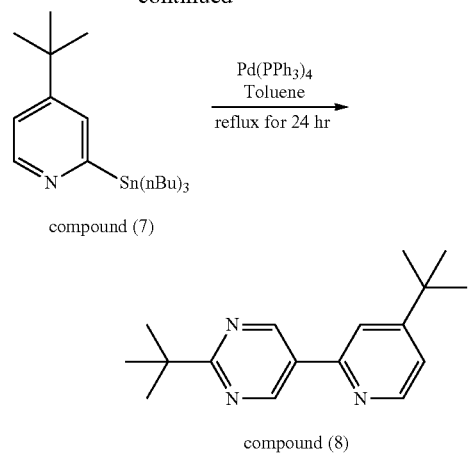

compound (7)

compound (8)

The physical measurement of the compound (8) is listed below: $^1$H NMR (400 MHz, CDCl$_3$, 294 K): δ 9.20 (s, 2H), 8.60 (d, $J_{HH}$=4.8 Hz, 1H), 7.64 (s, 1H), 7.69 (dd, $J_{HH}$=7.6, 2.0 Hz, 1H), 1.44 (s, 9H), 1.34 (s, 9H)

Next, 160 mg of compound (8) (0.59 mmol), 100 mg of IrCl$_3$·3H$_2$O (0.28 mmol), and 20 mL of 2-methoxyethanol were added into a reaction bottle, and then the mixture was heated to reflux for 12 hr under a nitrogen atmosphere. After cooling to room temperature, 90 mg of 2-(3-(trifluoromethyl)-1H-1,2,4-triazol-5-yl)pyrimidine (fppzH, with a structure of

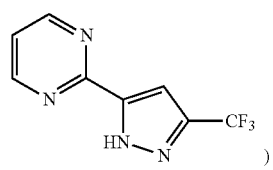

)

(0.42 mmol) and 150 mg of sodium carbonate (1.33 mmol) were added into the reaction bottle and heated to reflux for 4 hr. After cooling to room temperature, the solvent in the reaction bottle was removed, and then 20 ml of ethyl acetate was added into the bottle. After extracting by water, an organic phase was separated and dried by Na$_2$SO$_4$. After purification by column chromatography with ethyl acetate/hexane (3:1) as the extraction solvent and recrystallization, organometallic compound (II) (with a yield of 19%) and organometallic compound (III) (with a yield of 30%) were obtained. The synthesis pathway of the above reaction was as follows:

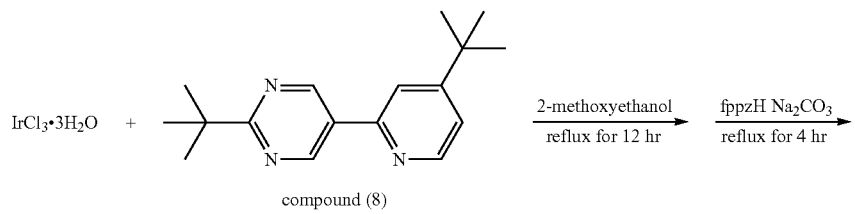

compound (8)

-continued

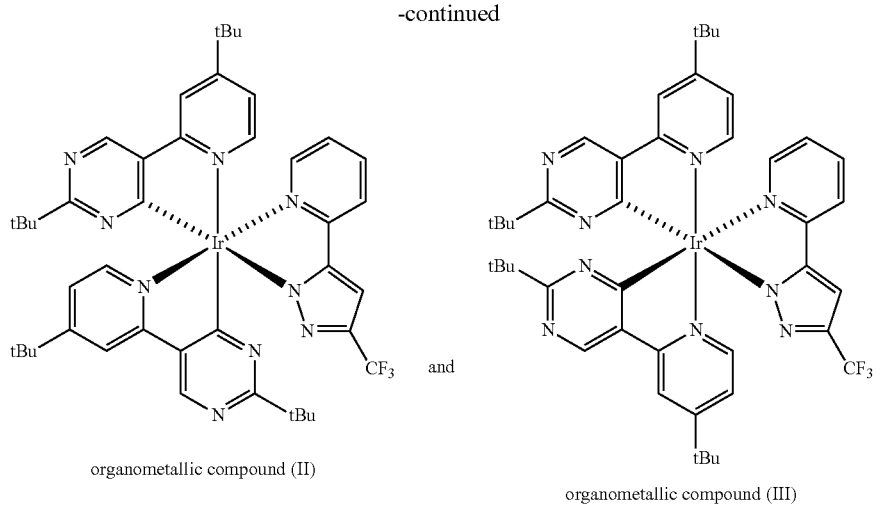

organometallic compound (II) and organometallic compound (III)

In addition, if the reflux time is increased from 4 hr to 20 hr, the reaction result would be organometallic compound (III) only.

The physical measurement of the organometallic compound (II) is listed below: $^1$H NMR (400 MHz, CDCl$_3$, 294 K): δ 8.49 (s, 1H), 8.45 (s, 1H), 7.90 (d, $J_{HH}$=6 Hz, 1H), 7.81 (s, 1H), 7.68~7.58 (m, 4H), 7.28~7.21 (m, 3H), 7.02~6.91 (m, 2H), 6.84 (t, $J_{HH}$=6.4 Hz, 1H), 1.33 (s, 9H), 1.28 (s, 9H), 1.12 (s, 9H), 1.09 (s, 9H); $^{19}$F-{$^1$H} NMR (376 MHz, CDCl$_3$, 294K): δ −59.80 (s, 3F). Fast atom bombardment mass spectrometry (FAB-MS): m/z: 943 [M$^{+2}$]$^+$. Elemental analysis: C$_{43}$H$_{49}$F$_3$IrN$_9$: N, 13.39; C, 54.88; H, 5.25. Found: N, 12.56; C, 54.72; H, 5.63.

The physical measurement of the organometallic compound (III) is listed below: $^1$H NMR (400 MHz, CDCl$_3$, 294 K): δ 8.40 (s, 1H), 8.39 (s, 1H), 7.76~7.70 (m, 4H), 7.65 (s, 1H), 7.60 (d, $J_{HH}$=6.4 Hz, 1H), 7.54 (d, $J_{HH}$=6 Hz, 1H), 7.89 (d, $J_{HH}$=6 Hz, 1H), 7.03~6.96 (m, 3H), 1.32 (s, 18H), 1.08 (s, 9H), 1.04 (s, 9H); $^{19}$F-{$^1$H} NMR (376 MHz, CDCl$_3$, 294K): δ −60.01 (s, 3F). Fast atom bombardment mass spectrometry (FAB-MS): m/z: 943 [M$^{+2}$]$^+$. Elemental analysis: C$_{43}$H$_{49}$F$_3$IrN$_9$: N, 13.39; C, 54.88; H, 5.25. Found: N, 12.86; C, 55.24; H, 5.38.

Example 3: Preparation of Organometallic Compounds (IV) and (V)

0.44 g of sodium ethoxide (6.45 mmol)), 0.53 g of compound 1 (tert-butylcarbamidine hydrochloride) (3.87 mmol), and 10 mL of ethanol were added into a reaction bottle. After stirring, 0.5 g of compound (9) ((E)-1-(4-tert-butylpyridin-2-yl)-3-(dimethylamino)prop-2-en-1-one (II) (2.15 mmol)) was added into the reaction bottle. After heating to reflux for 3 hr, HCl (2N) was added into the reaction bottle to adjust the pH value to 7.0. After concentrating and purification by column chromatography, compound (10) (2-tert-butyl-4-(4-tert-butylpyridin-2-yl)pyrimidine) was obtained with a yield of 90%. The synthesis pathway of the above reaction was as follows:

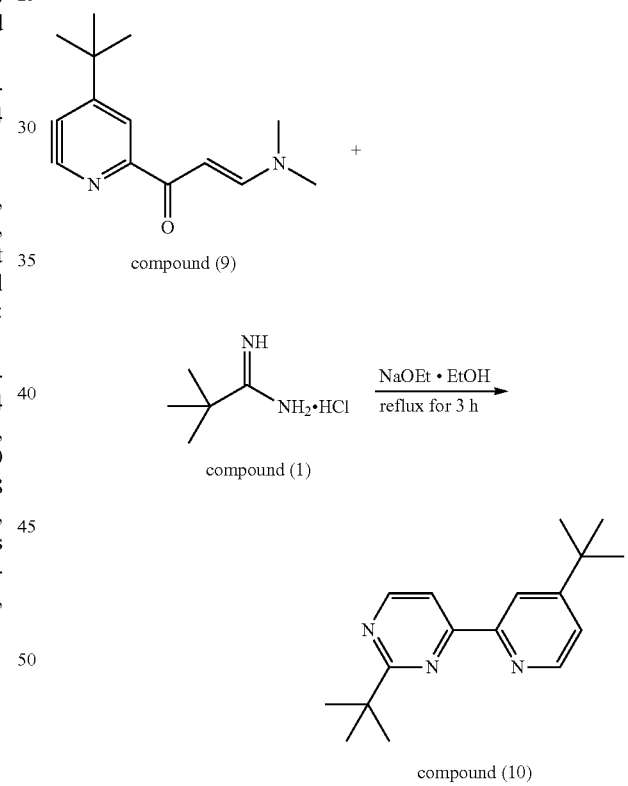

compound (9)

compound (1)

NaOEt • EtOH
reflux for 3 h compound (10)

The physical measurement of the compound (10) is listed below: 1H NMR: (400 MHz, CDCl3, 294 K): δ 8.78 (d, $J_{HH}$=5.2 Hz, 1H), 8.60~8.58 (m, 2H), 8.09 (d, $J_{HH}$=5.2 Hz, 1H), 7.36 (d, $J_{HH}$=4 Hz, 1H), 1.48 (s, 9H), 1.38 (s, 9H).

Next, 241 mg of compound (10) (0.89 mmol), 150 mg of IrCl$_3$.3H$_2$O (0.43 mmol), and 20 mL of 2-methoxyethanol were added into a reaction bottle. After heating to reflux for 12 hr and then cooling to room temperature, 136 mg of 2-(3-(trifluoromethyl)-1H-1,2,4-triazol-5-yl)pyrimidine (fp-pzH, with a structure of

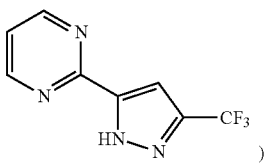

(0.64 mmol) and 226 mg of sodium carbonate (2.13 mmol) were added into the reaction bottle. After heating to reflux 4 hr and cooling to room temperature, the solvent in the reaction bottle was removed, and then 20 mL of ethyl acetate was added into the reaction bottle. After extracting by water, an organic phase was separated and dried by $Na_2SO_4$, obtaining organometallic compound (IV) (with a yield of 30%) and organometallic compound (V) (with a yield of 20%). The synthesis pathway of the above reaction was as follows:

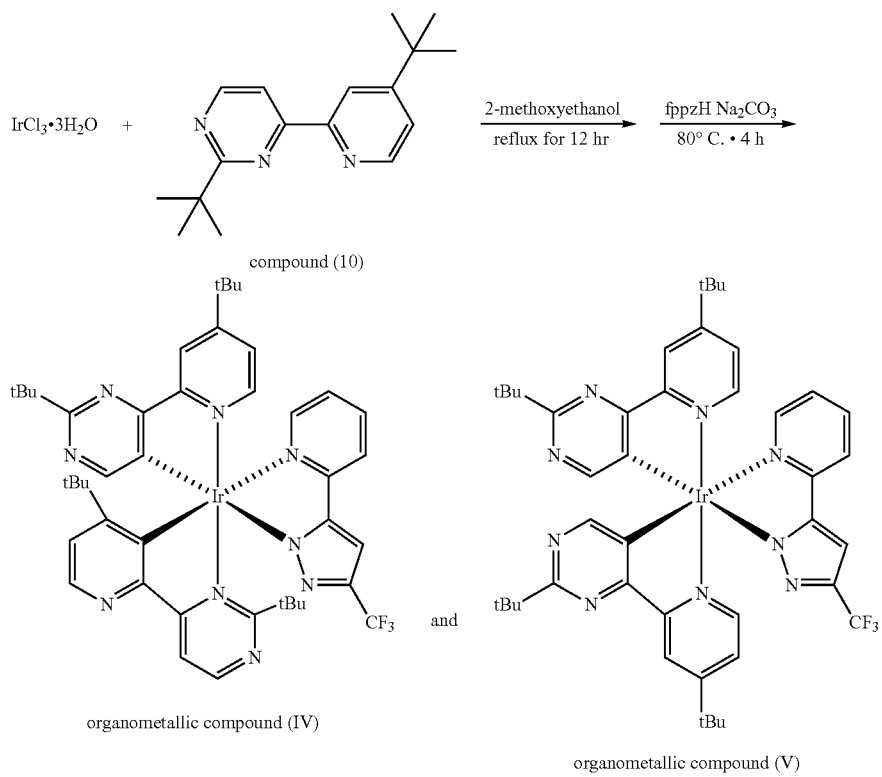

The physical measurement of the organometallic compound (IV) is listed below: $^1$H NMR (400 MHz, $CDCl_3$, 294 K): δ 8.38 (d, $J_{HH}$=2.4 Hz, 1H), 8.31 (d, $J_{HH}$=2 Hz, 1H), 7.85 (d, $J_{HH}$=5.6 Hz, 1H), 7.79~7.74 (m, 3H), 7.67 (s, 1H), 7.47~7.43 (m, 2H), 7.16 (dd, $J_{HH}$=8.0, 2.4 Hz, 1H), 7.07~7.01 (m, 2H), 6.95 (s, 1H), 1.39 (s, 9H), 1.37 (s, 9H), 1.35 (s, 9H), 1.33 (s, 9H); $^{19}$F-{$^1$H} NMR (376 MHz, $CDCl_3$, 294K): δ −59.98 (s, 3F). Fast atom bombardment mass spectrometry (FAB-MS): m/z: 943 [$M^{+2}$]$^+$. Elemental analysis: $C_{43}H_{49}F_3IrN_9$: N, 13.39; C, 54.88; H, 5.25. Found: N, 12.94; C, 53.62; H, 5.39.

The physical measurement of the organometallic compound (V) is listed below: $^1$H NMR (400 MHz, $CDCl_3$, 294 K): δ 8.50 (d, $J_{HH}$=2 Hz, 1H), 8.33 (d, $J_{HH}$=2 Hz, 1H), 8.06 (s, 1H), 7.90 (d, $J_{HH}$=6 Hz, 1H), 7.84 (s, 1H), 7.64 (d, $J_{HH}$=4.8 Hz, 2H), 7.45 (d, $J_{HH}$=6 Hz, 1H), 7.39 (d, $J_{HH}$=5.6 Hz, 1H), 7.33 (dd, $J_{HH}$=8, 2.4 Hz, 1H), 7.33 (dd, $J_{HH}$=8, 2.4 Hz, 1H), 7.03 (dd, $J_{HH}$=8.4, 2.0 Hz, 1H), 6.95 (s, 1H), 6.86~6.83 (m, 1H), 1.40 (s, 9H), 1.39 (s, 9H), 1.38 (s, 9H), 1.33 (s, 9H); $^{19}$F-{$^1$H} NMR (376 MHz, $CDCl_3$, 294K): δ −59.89 (s, 3F). Fast atom bombardment mass spectrometry (FAB-MS): m/z: 943 [$M^{+2}$]$^+$. Elemental analysis: $C_{43}H_{49}F_3IrN_9$: N, 13.39; C, 54.88; H, 5.25. Found: N, 12.67; C, 54.45; H, 5.63.

Example 4: Preparation of Organometallic Compound (VI)

Next, 68 mg of compound (8) (0.25 mmol), 130 mg of $IrCl_3 \cdot 3H_2O$ (0.23 mmol), 64 mg $PPh_3$ (triphenylphosphine) (0.24 mmol)), and 13 ml of decahydronaphthalene were added into a reaction bottle. After heating to 120° C. for 6 hr and cooling to room temperature, 103 mg of 2-(3-(trifluoromethyl)-1H-1,2,4-triazol-5-yl)pyrimidine (fppzH, with a structure of

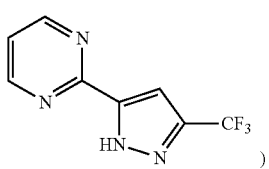

(0.49 mmol) and 122 mg of sodium carbonate (1.2 mmol) were added into the reaction bottle. After heating to reflux for 20 hr and cooling to room temperature, the solvent in the reaction bottle was removed, and then 20 mL of ethyl acetate was added into the reaction bottle. After extracting by water, an organic phase was separated and dried by $Na_2SO_4$. After purification by column chromatography with ethyl acetate/hexane (5:1) as the extraction solvent, organometallic compound (VI) (with a yield of 37%) was obtained. The synthesis pathway of the above reaction was as follows:

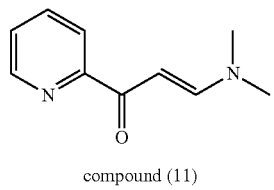

compound (11)

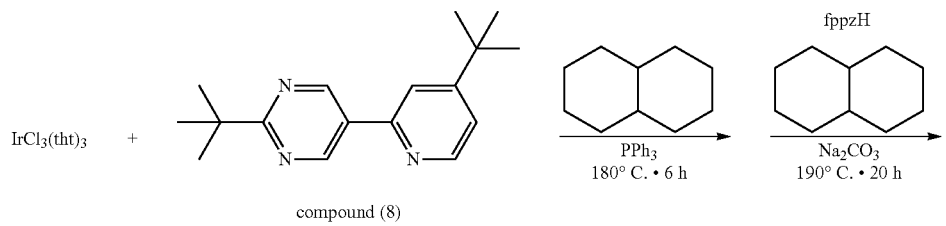

compound (8)

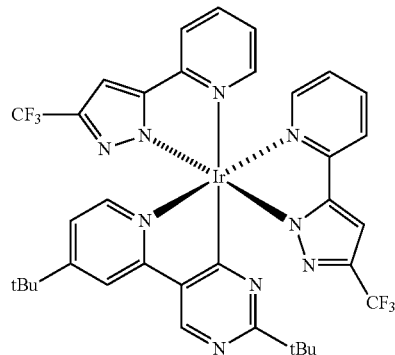

organometallic compound (VI)

The physical measurement of the organometallic compound (VI) is listed below: $^1$H NMR (400 MHz, CDCl$_3$, 294 K): 8.48 (s, 1H), 7.84~7.72 (m, 4H), 7.62 (d, $J_{HH}$=8 Hz, 1H), 7.55 (d, $J_{HH}$=6 Hz, 1H), 7.43 (t, $J_{HH}$=6 Hz, 2H), 7.17 (t, $J_{HH}$=6.4 Hz, 1H), 7.01~6.98 (m, 2H), 6.88 (s, 1H), 6.86 (s, 1H), 1.33 (s, 9H), 1.07 (s, 9H); $^{19}$F-{$^1$H} NMR (376 MHz, CDCl$_3$, 294K): δ59.75 (s, 3F), 60.02 (s, 3F). Fast atom bombardment mass spectrometry (FAB-MS): m/z: 885 [M$^{+2}$]$^+$. Elemental analysis: C35H32F6IrN9: N, 14.25; C, 47.51; H, 3.64. Found: N, 13.96; C, 47.18; H, 4.00.

Example 5: Preparation of Organometallic Compound (VII)

12.7 g of 2-acetylpyridine (10.48 mmole) and 13.33 g of N,N-dimethylformamide dimethyl acetal (DMFDMA) (11.2 mmole) were added into a reaction bottle. The mixture was heated to reflux (120° C.) for 4.5 hr, and then the reaction bottle was cooled to room temperature. After recrystallization by ethyl acetate, compound (11) was obtained with a yield of 88%. The synthesis pathway of the above reaction was as follows:

The physical measurement of the compound (11) is listed below: $^1$H-NMR: (500 MHz, CDCl$_3$, 298 K): δ 8.61 (d, $J_{HH}$=5.2 Hz, 1H), 8.13 (d, $J_{HH}$=8 Hz, 1H), 7.90 (d, $J_{HH}$=12.8 Hz, 1H), 7.79 (td, $J_{HH}$=7.6, 2 Hz, 1H), 7.35 (ddd, $J_{HH}$=7.8, 4.8, 1.2 Hz, 1H), 6.44 (d, $J_{HH}$=12.4 Hz, 1H), 3.16 (s, 3H), 2.98 (s, 3H).

Next, 5 g of compound (11) (28.37 mmole), 5.72 g of trifluoroacetamidine (51.05 mmole), and 50 mL of ethanol were added into a reaction bottle. After stirring at room temperature for 20 min, 3.86 g of sodium ethoxide (56.74 mmole) was added into the reaction bottle, and then the mixture was heated to reflux for 2 hr. After cooling to room temperature, HCl (aq) (2N) was added into the reaction bottle to adjust the pH value to 7.0 at 0° C. After purification by column chromatography, compound (12) as a light yellow solid was obtained with a yield of 94%. The synthesis pathway of the above reaction was as follows:

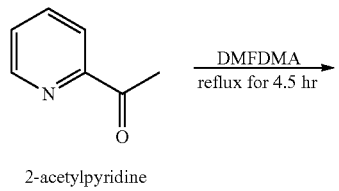

2-acetylpyridine

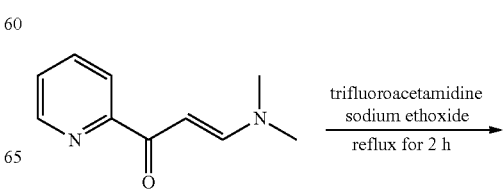

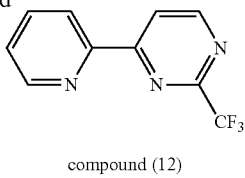

compound (12)

The physical measurement of the compound (12) is listed below: $^{1}$H-NMR: (400 MHz, CDCl$_3$, 298 K): δ 8.99 (d, $J_{HH}$=5.2 Hz, 1H), 8.73 (d, $J_{HH}$=4.8 Hz, 1H), 8.58 (d, $J_{HH}$=8.0 Hz, 1H), 8.55 (d, $J_{HH}$=5.2 Hz, 1H), 7.89 (td, $J_{HH}$=7.6 Hz, $J_{HH}$=0.8 Hz, 1H), 7.45 (ddd, $J_{HH}$=7.6, 4.8, 0.8 Hz, 1H).

Fast atom bombardment mass spectrometry (FAB-MS): m/z 225 [M]

Next, 0.135 g of compound (12) (0.60 mmol), 100 mg of IrCl$_3$.3H$_2$O (0.28 mmol), and 20 mL of 2-methoxyethanol were added into a reaction bottle, and the mixture was heated to reflux for 4 hr. After cooling to room temperature, 0.65 g of 2-(3-(trifluoromethyl)-1H-1,2,4-triazol-5-yl)pyrimidine (fppzH, with a structure of

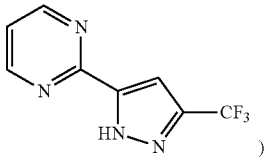

(2.8 mmol) and 0.3 g of sodium carbonate (2.8 mmol) were added into a reaction bottle, and then the mixture was heated to reflux for 1 hr. After cooling to room temperature, the solvent in the reaction bottle was removed, and then 20 mL of dichloromethane was added into the reaction bottle. After extracting by water, an organic phase was separated and dried by Na$_2$SO$_4$.

After purification by column chromatography with ethyl acetate as the extraction solvent and recrystallization, organometallic compound (VII) was obtained with a yield of 38%. The synthesis pathway of the above reaction was as follows:

IrCl$_3$·3H$_2$O +

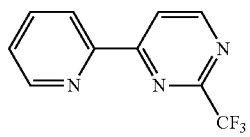

compound (12)

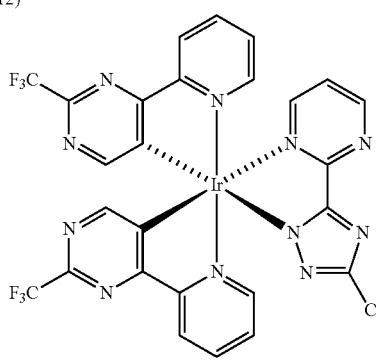

organometallic compound (VII)

The physical measurement of the organometallic compound (VII) is listed below: $^{1}$H NMR (400 MHz, CDCl$_3$, 294 K): δ 9.06~9.04 (m, 1H), 8.58 (d, $J_{HH}$=8.0 Hz, 1H), 8.54 (d, $J_{HH}$=8.0 Hz, 1H), 8.03~7.99 (m, 3H), 7.95 (s, 1H), 7.83 (d, $J_{HH}$=5.6 Hz, 1H), 7.79 (s, 1H), 7.66 (d, $J_{HH}$=5.2 Hz, 1H), 7.42 (t, $J_{HH}$=6.4 Hz, 1H), 7.35~7.31 (m, 2H). Fast atom bombardment mass spectrometry (FAB-MS): m/z 856 [M$^{++1}$].

Example 6: Preparation of Organometallic Compound (VIII)

0.135 g of compound (12) (0.60 mmol), 0.10 g of IrCl$_3$.3H$_2$O (0.28 mmol), and 20 mL of 2-methoxyethanol were added into a reaction bottle, and the mixture was heated to reflux for 4 hr under a nitrogen atmosphere. After cooling to room temperature, 61 mg of 2-(3-tert-butyl-1H-1,2,4-triazol-5-yl) pyridine (with a structure of

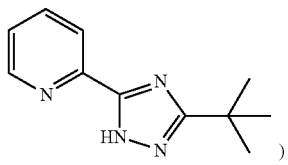

)

(0.30 mmole) and 0.636 g of sodium carbonate (6 mmole) was added into the reaction bottle, and then the mixture was heated to reflux for 3 hr. After cooling to room temperature, the solvent in the reaction bottle was removed, and 20 mL of ethyl acetate was added into the reaction bottle. After washing by water, an organic phase was separated and dried by Na$_2$SO$_4$.

After purification by column chromatography with ethyl acetate as the extraction solvent and recrystallization, organometallic compound (VIII) was obtained with a yield of 74%. The synthesis pathway of the above reaction was as follows:

IrCl$_3$·3H$_2$O +

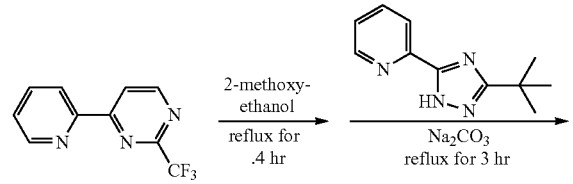

compound (12)

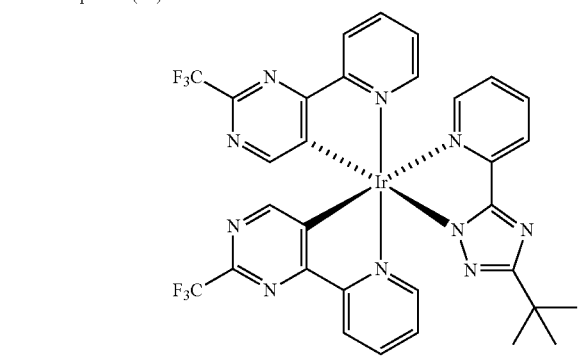

organometallic compound (VIII)

The physical measurement of the organometallic compound (VIII) is listed below: $^1$H NMR (400 MHz, CDCl$_3$, 294 K): δ 8.51~8.46 (m, 2H), 8.27 (d, J$_{HH}$=8.0 Hz, 1H), 7.94~7.87 (m, 4H), 7.83 (s, 1H), 7.74 (d, J$_{HH}$=5.6 Hz, 1H), 7.68 (d, J$_{HH}$=5.6 Hz, 1H), 7.63 (d, J$_{HH}$=5.6 Hz, 1H), 7.30 (t, J$_{HH}$=6.0 Hz, 1H), 7.24 (t, J$_{HH}$=6.0 Hz, 1H), 7.16 (t, J$_{HH}$=6.0 Hz, 1H), 1.33 (s, 9H). Fast atom bombardment mass spectrometry (FAB-MS): m/z 841 [M++1].

Example 7: Preparation of Organometallic Compound (IX)

0.135 g of compound (12) (0.60 mmol), 0.10 g of IrCl$_3$.3H$_2$O (0.28 mmol), and 20 mL of 2-methoxyethanol were added into a reaction bottle, and then the mixture was heated to reflux for 4 hr under a nitrogen atmosphere. After cooling to room temperature, 61 mg of 2-(3-tert-butyl-1H-1,2,4-triazol-5-yl)pyrimidine, with a structure of

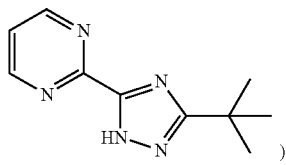

)

(0.30 mmole) and 0.636 g of sodium carbonate (6 mmole) were added into the reaction bottle. After heating to reflux for 3 hr and then cooling to room temperature, the solvent in the reaction bottle was removed, and 20 mL of dichloromethane was added into the reaction bottle. After washing by water, an organic phase was separated and dried by Na$_2$SO$_4$. After purification by column chromatography with ethyl acetate/MeOH (2:1) as the extraction solvent and recrystallization, organometallic compound (IX) was obtained with a yield of 60%. The synthesis pathway of the above reaction was as follows:

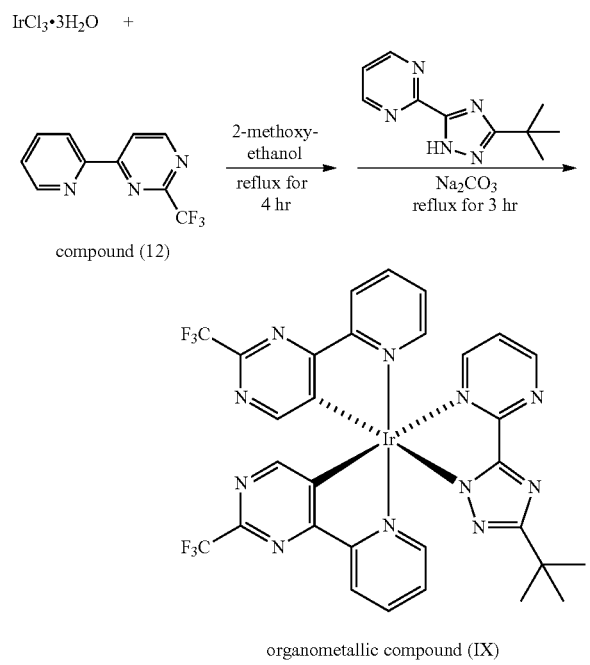

organometallic compound (IX)

The physical measurement of the organometallic compound (IX) is listed below: $^1$H NMR (400 MHz, CDCl$_3$, 294 K): δ 8.94~8.92 (m, 1H), 8.52 (d, J$_{HH}$=7.6 Hz, 1H), 8.49 (d, J$_{HH}$=8.0 Hz, 1H), 7.96~7.92 (m, 4H), 7.80 (s, 1H), 7.72 (d, J$_{HH}$=6.5 Hz, 1H), 7.70 (d, J$_{HH}$=5.6 Hz, 1H), 7.35 (t, J$_{HH}$=6.0 Hz, 1H), 7.28 (t, J$_{HH}$=6.0 Hz, 1H), 7.14 (t, J$_{HH}$=5.2 Hz, 1H), 1.34 (s, 9H). Fast atom bombardment mass spectrometry (FAB-MS): m/z 843 [M++1].

Example 8: Preparation of Organometallic Compound (X)

0.135 g of compound (12) (0.60 mmol), 0.10 g of IrCl$_3$.3H$_2$O (0.28 mmol), and 20 mL of 2-methoxyethanol were added into a reaction bottle, and then the mixture was heated to reflux for 4 hr under a nitrogen atmosphere. After cooling to room temperature, 61 mg of 2-(3-tert-butyl-1H-pyrazol-5-yl)pyrazine (with a structure of

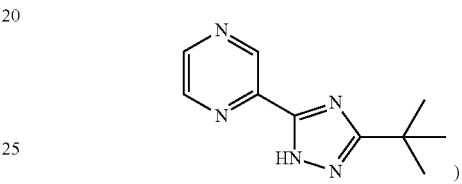

)

(0.30 mmole) and sodium carbonate (0.636 g, 6 mmole) were added into the reaction bottle, and then the mixture was heated to reflux for 3 hr. After cooling to room temperature, the solvent in the reaction bottle was removed, and then 20 mL of dichloromethane was added into the reaction bottle. After extracting by water, an organic phase was separated and dried by Na$_2$SO$_4$. After purification by column chromatography with ethyl acetate/MeOH (2:1) as the extraction solvent and recrystallization, organometallic compound (X) was obtained with a yield of 62%. The synthesis pathway of the above reaction was as follows:

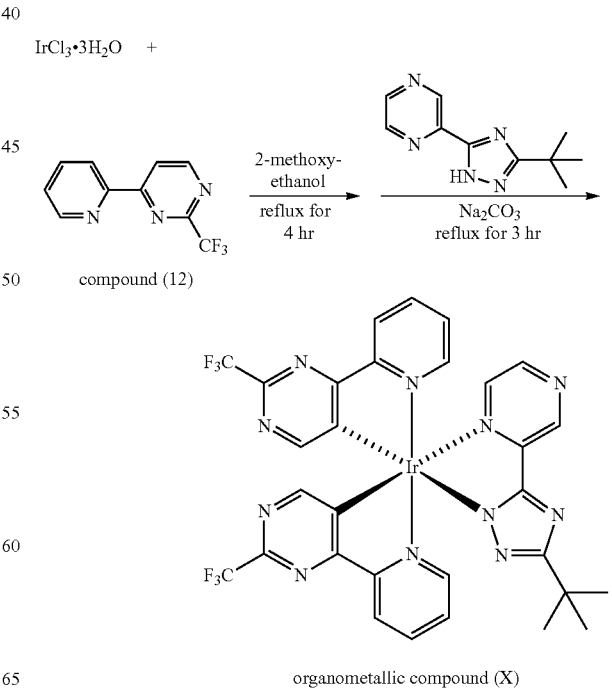

organometallic compound (X)

The physical measurement of the organometallic compound (X) is listed below: $^1$H NMR (400 MHz, CDCl$_3$, 294 K): δ 9.03 (s, 1H), 8.47 (t, $J_{HH}$=8.0 Hz, 2H), 8.17 (d, $J_{HH}$=2.8 Hz, 1H), 7.96 (s, 1H), 7.92~7.86 (m, 2H), 7.80 (s, 1H), 7.75 (d, $J_{HH}$=5.6 Hz, 1H), 7.60 (d, $J_{HH}$=1.6 Hz, 1H), 7.40 (d, $J_{HH}$=5.6 Hz, 1H), 7.25 (d, $J_{HH}$=5.6 Hz, 1H), 6.61 (s, 1H), 1.23 (s, 9H). Fast atom bombardment mass spectrometry (FAB-MS): m/z 843 [M$^{++1}$].

The ultraviolet absorption spectra and photoluminescence excitation spectra of the organometallic compound (I) and organometallic compound (III) were measured, and the result was shown in FIG. 1. The structural differences between the organometallic compound (I) and organometallic compound (III) is that there is a t-butyl group bonded at the 4-position of the pyridyl moiety of organometallic compound (III). Therefore, the organometallic compound (III) has an improved thermal stability and a reduced extinction coefficient due to the increased steric hindrance.

Due to the similar structure, there was no significant difference between the ultraviolet absorption spectra (or photoluminescence excitation spectra) of the organometallic compound (I) and organometallic compound (III). In the photoluminescence excitation spectra of the organometallic compound (I) and organometallic compound (III), the major peaks are 456 nm and 457 nm respectively. On the other hand, the major peak in the photoluminescence excitation spectrum of the conventional blue phosphorescent material FIrpic is about 475 nm. Therefore, in comparison with FIrpic, the emission wavelength range (with a blue shift of about 20 nm) of the organometallic compound of the disclosure is closer to standard blue (NTSC blue).

Figure 2:
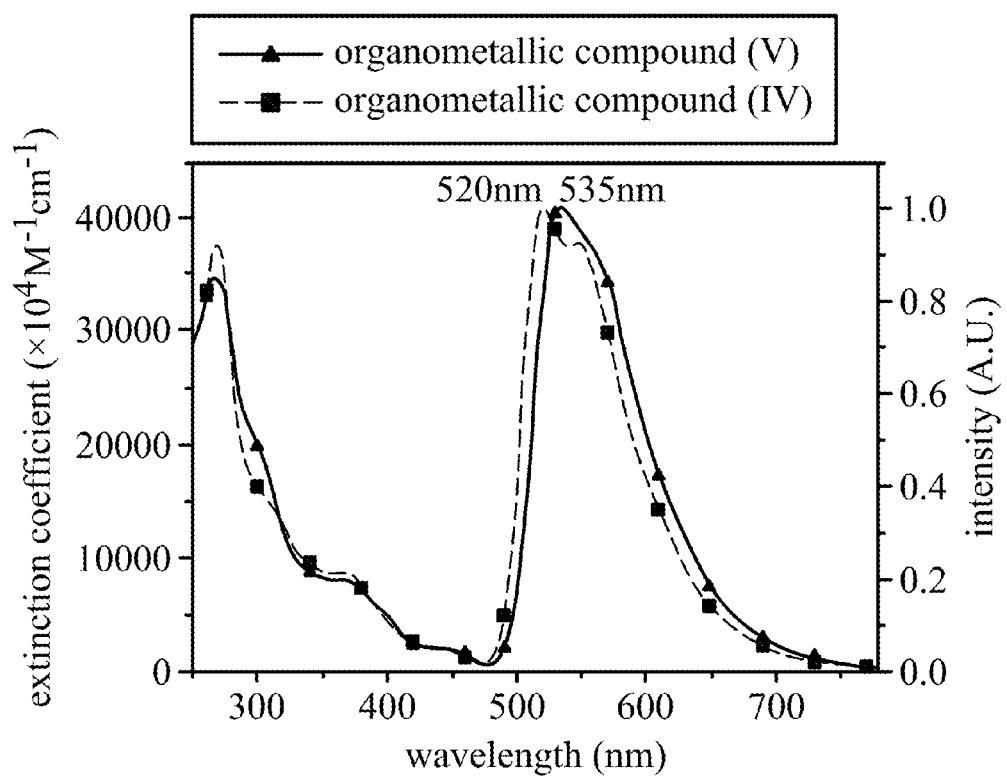
FIG. 2 shows ultraviolet absorption spectra and photoluminescence excitation spectra of the organometallic compounds (IV) and (V) of the disclosure.

The ultraviolet absorption spectra and photoluminescence excitation spectra of the organometallic compound (IV) and organometallic compound (V) were measured, and the result is shown in FIG. 2. Since the position of the two nitrogen atoms of the pyrimidinyl moiety is changed resulting in varying the charge density of the ligand, the organometallic compound (IV) and organometallic compound (V) have different HOMO and LUMO energy gaps in comparison with compound (I) and organometallic compound (II) and can serve as green phosphorescent materials.

Figure 3:
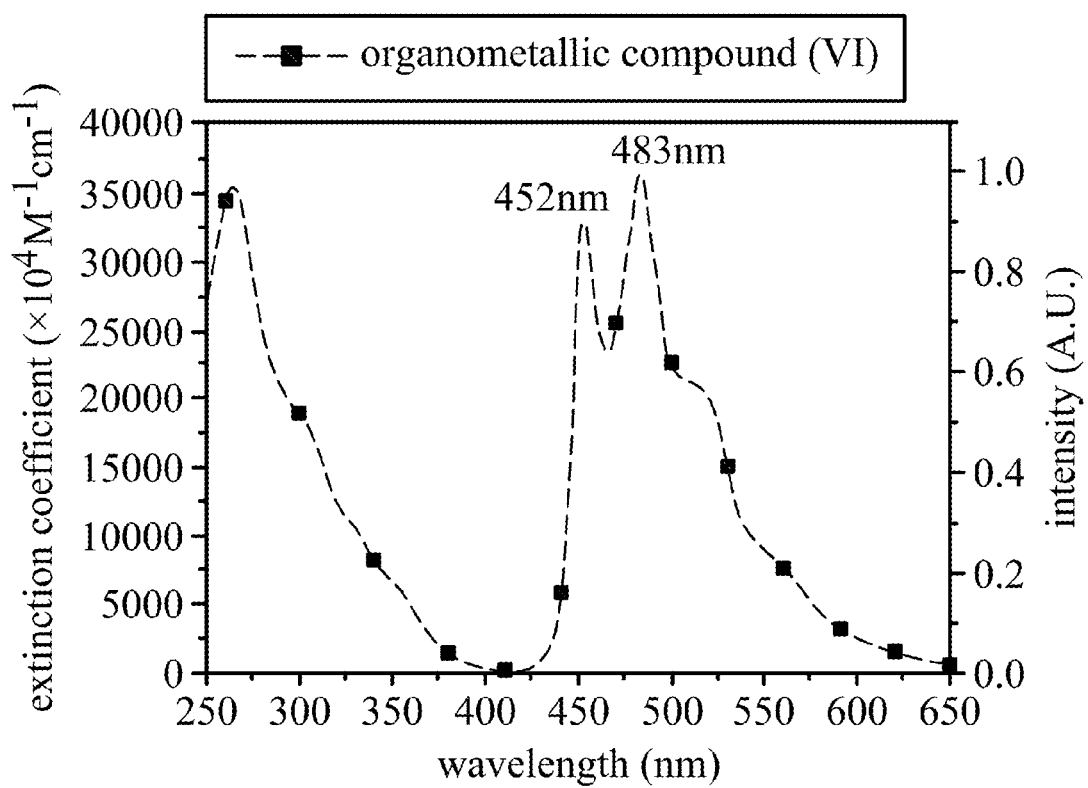
FIG. 3 shows ultraviolet absorption spectrum of the organometallic compounds (VI) of the disclosure.

The ultraviolet absorption spectrum and photoluminescence excitation spectrum of the organometallic compound (VI) was measured, and the result was shown in FIG. 3. Since the major peak in the photoluminescence excitation spectrum of the compound (VI) is about 483 nm, the compound (VI) can serve as a blue phosphorescent material.

The oxidation potential ($E^{ox}$) and the reduction potential ($E^{re}$) of the organometallic compounds (I), (III), (V) and (VI) were measured, and the results are shown in Table 1. The HOMO and LUMO energy gaps of the organometallic compounds (I), (III), (V) and (VI), measured from the oxidation and reduction potentials, correspond to the blue or green phosphorescent dopant.

TABLE 1

|  | $E^{ox}$(V) | $E^{re}$(V) [ΔEp] |
|---|---|---|
| organometallic compound (I) | 1.04 [irr] | −2.75 [irr] |
| organometallic compound (III) | 1.00 [irr] | −2.71 [0.13] |
| organometallic compound (V) | 0.83 [irr] | −2.34 [0.11] |
| organometallic compound (VI) | 1.13 [irr] | −2.70 [irr] |

Organic Light-Emitting Device

Figure 4:
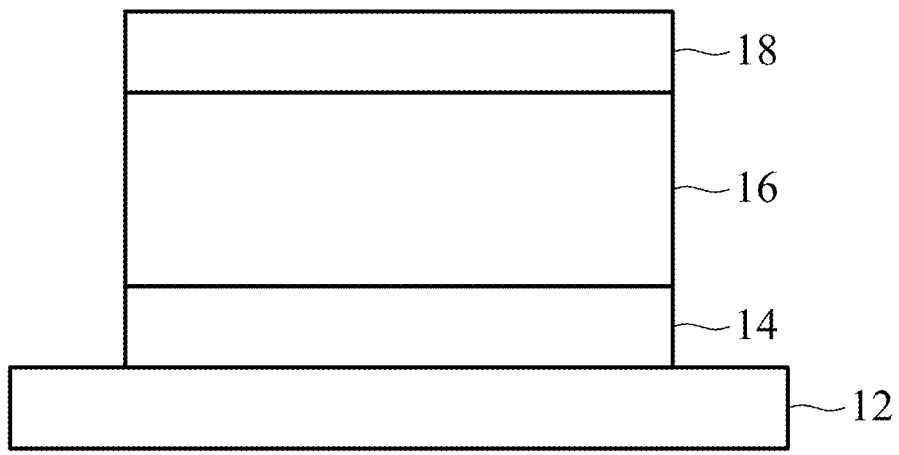
FIG. 4 shows a cross section of an organic light-emitting device disclosed by an embodiment of the disclosure.

FIG. 4 shows an embodiment of an organic light-emitting device 10. The organic light-emitting device 10 includes a substrate 12, a bottom electrode 14, an electroluminescent element 16, and a top electrode 18, as shown in FIG. 4. The organic light-emitting device can be top-emission, bottom-emission, or dual-emission devices. The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent. The electroluminescent element 16 at least includes an emission layer, and can further include a hole injection layer, a hole transport layer, an electron transport layer, and an electron injection layer. In an embodiment of the disclosure, at least one layer of the electroluminescent element 16 includes the aforementioned organometallic compound. According to embodiments of the disclosure, the electroluminescent element 16 can emit blue or green light under a bias voltage. According to another embodiment of the disclosure, the organic light-emitting device can be a phosphorescent organic light-emitting device, and the emission layer of the electroluminescent element can include a host material and a dopant, wherein the dopant can include the aforementioned organic compounds. The dose of the dopant is not limited and can be optionally modified by a person of ordinary skill in the field.

In order to clearly disclose the organic light-emitting devices of the disclosure, the following examples (employing the organometallic compounds of the disclosure) are intended to illustrate the disclosure more fully without limiting their scope, since numerous modifications and variations will be apparent to those skilled in this art.

Example 9: Organic Light-Emitting Device (1)

A glass substrate with an indium tin oxide (ITO) film with a thickness of 110 nm was provided and then washed with a cleaning agent, acetone, and isopropanol with ultrasonic agitation. After drying with nitrogen flow, the ITO film was subjected to a UV/ozone treatment for 30 min Next, TAPC (1,1-bis[4-[N,N'-di(p-tolyl)amino]phenyl]cyclohexane, with a thickness of 30 nm), TCTA (4,4',4'-tri(N-carbazolyl) triphenylamine), with a thickness of 10 nm), mCP (N,N'-dicarbazolyl-3,5-dibenzene, with a thickness of 3 nm), mCP doped with the organometallic compound (III) of Example 2 (the ratio between mCP and the organometallic compound (III) was 100:6, with a thickness of 25 nm), UGH2 (1,4-bis (triphenylsilyl)benzene) doped with the organometallic compound (III) of Example 2 (the ratio between UGH2 and the organometallic compound (III) was 100:6, with a thickness of 3 nm), UGH2 (with a thickness of 2 nm), TmPyPB (1,3,5-tri(p-pyrid-3-yl-phenyl)benzene, with a thickness of 30 nm), LiF (with a thickness of 0.5 nm), and Al (with a thickness of 120 nm) were subsequently formed on the ITO film at 10-6 torr, obtaining the organic light-emitting device (1). The materials and layers formed therefrom are described in the following: ITO/TAPC/TCTA/mCP:organometallic compound (III) (6%)/UGH2:organometallic compound (III) (6%)/UGH2/TmPyPB/LiF/Al Next, the optical properties of the light-emitting device (1), as described in Example 9, were measured by a spectra colorimeter PR650 (purchased from Photo Research Inc.) and a luminance meter LS110 (purchased from Konica Minolta). The results are shown in Table 2.

Example 10: Organic Light-Emitting Device (2)

Example 10 was performed in the same manner as in Example 9 except that BmPyPB (with a structure of

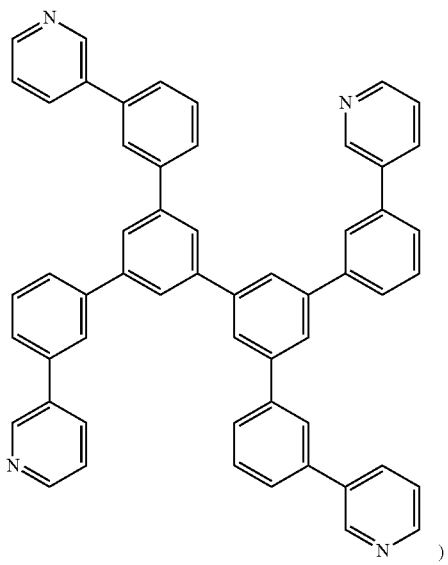

was substituted for TmPyPB, obtaining the organic light-emitting device (2). The materials and layers formed therefrom are described in the following: ITO/TAPC/TCTA/mCP:organometallic compound (III) (6%)/UGH2:organometallic compound (III) (6%)/UGH2/BmPyPB/LiF/Al Next, the optical properties of the light-emitting device (2), as described in Example 10, were measured by a spectra colorimeter PR650 (purchased from Photo Research Inc.) and a luminance meter LS110 (purchased from Konica Minolta). The results are shown in Table 2.

Example 11: Organic Light-Emitting Device (3)

Example 11 was performed in the same manner as in Example 9 except that TCTA layer was removed, and the thickness of the TAPC layer was increased from 30 nm to 40 nm, obtaining the organic light-emitting device (3). The materials and layers formed therefrom are described in the following: ITO/TAPC/mCP:organometallic compound (III) (6%)/UGH2:organometallic compound (III) (6%)/UGH2/TmPyPB/LiF/Al Next, the optical properties of the light-emitting device (3), as described in Example 11, were measured by a spectra colorimeter PR650 (purchased from Photo Research Inc.) and a luminance meter LS110 (purchased from Konica Minolta). The results are shown in Table 2.

Example 12: Organic Light-Emitting Device (4)

Example 12 was performed in the same manner as in Example 10 except that TCTA layer was removed, and the thickness of the TAPC layer was increased from 30 nm to 40 nm, obtaining the organic light-emitting device (4). The materials and layers formed therefrom are described in the following: ITO/TAPC/mCP:organometallic compound (III) (6%)/UGH2:organometallic compound (III) (6%)/UGH2/BmPyPB/LiF/Al Next, the optical properties of the light-emitting device (4), as described in Example 12, were measured by a spectra colorimeter PR650 (purchased from Photo Research Inc.) and a luminance meter LS110 (purchased from Konica Minolta). The results are shown in Table 2.

In addition, a light-emitting device disclosed in Example 17 of JP2008074831A (the materials and layers formed therefrom are described in the following: ITO/TPDPSE: 10 wt % TBPAH/3DTAPBP/4CzPBP: 5 wt % (Bppm)$_2$IR(Bpypz)/BmPyPB/LiF/Al) serves as a comparative example. The optical properties of the comparative example are also shown in Table 2.

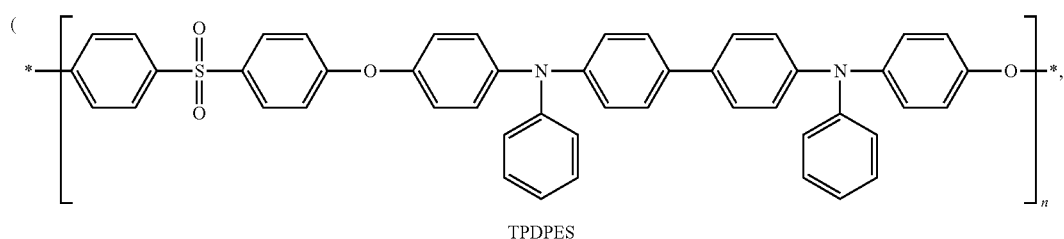

TPDPES

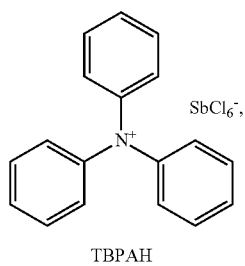

TBPAH

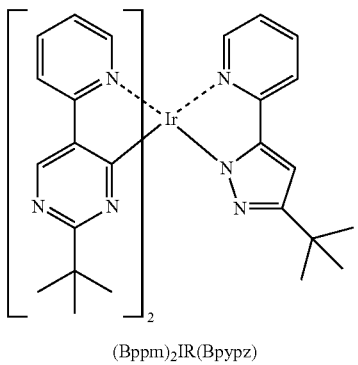

(Bppm)$_2$IR(Bpypz)

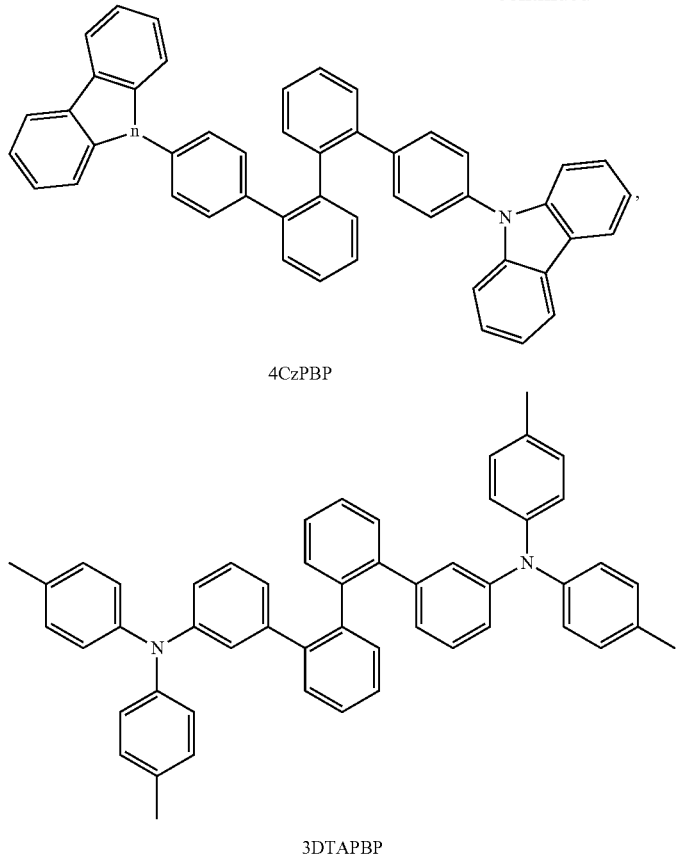

4CzPBP

3DTAPBP ).

TABLE 2

| | measured at a brightness of 100 Cd/m² | | | | C.I.E | |
|---|---|---|---|---|---|---|
| | external quantum efficiency (%) | current efficiency (cd/A) | power efficiency (lm/W) | driving voltage (V) | (measured at a brightness of 1000 Cd/m²) | maximum brightness (cd/m²) |
| organic light-emitting device (1) | 15.58 | 32.6 | 20.67 | 3.89 | (0.186, 0.315) | 14026 |
| organic light-emitting device (2) | 13.68 | 28.28 | 17.87 | 4.03 | (0.184, 0.312) | 12827 |
| organic light-emitting device (3) | 15.85 | 33.65 | 21.62 | 3.58 | (0.189, 0.322) | 15538 |
| organic light-emitting device (4) | 15.10 | 31.86 | 20.95 | 3.76 | (0.188, 0.320) | 16014 |
| comparative example | 6.8 | — | 13.6 | — | — | — |

As shown in Table 2, the organometallic compound of the disclosure can serve as phosphorescent dopant of organic light-emitting devices for increasing the luminescent efficiency.

Figure 5:
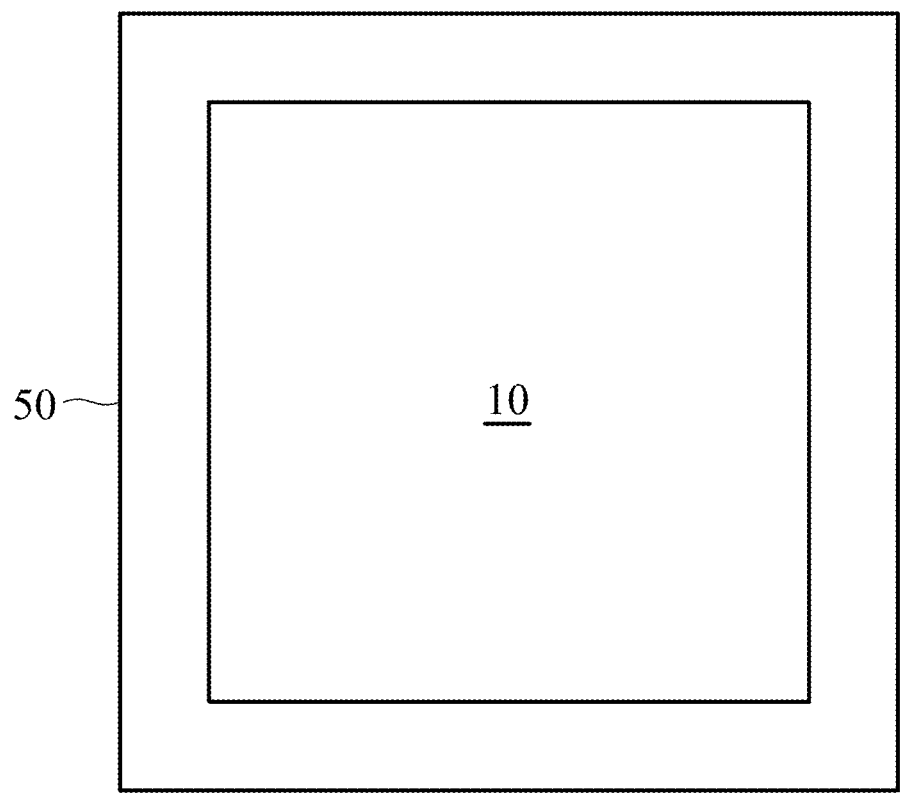
FIG. 5 schematically shows a block diagram of a lighting device according to an embodiment of the disclosure.

FIG. 5 schematically shows a block diagram of a lighting device 100 according to an embodiment of the disclosure. For example, the lighting device 100 can be an indoor lighting, a street lighting, a car lighting, or a back light source of a display device. The lighting device 100 of the disclosure can include the aforementioned organic light-emitting device 10 and a lead frame 50. In particular, the organic light-emitting device 10 is fixed on the lead frame 50, and the organic light-emitting device 10 connects to a power via the lead frame 50.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organometallic compound having a Formula (I) or Formula (II), of:

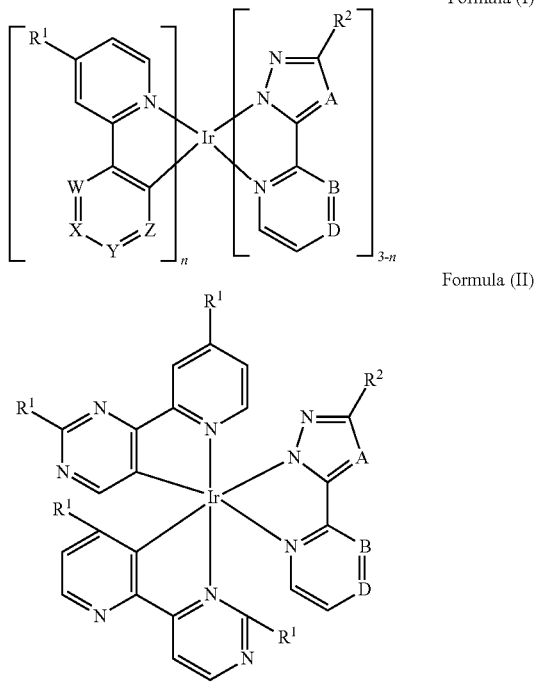

wherein, n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl, or $C_{1-8}$ alkyl; A is N, or CH; B is N, or CH; D is N, or C—$R^3$, wherein $R^3$ is H, or $C_{1-8}$ alkyl; and $R^1$ is not hydrogen when $R^2$ is hydrogen, and wherein one of following two conditions (1) and (2) is met: (1) X and Z are N, W is CH, Y is C—$R^4$, wherein $R^4$ is hydrogen, $C_{1-8}$ alkyl, $C_{1-8}$ fluoroalkyl, $C_{1-8}$ alkoxy, $C_{5-10}$ aryl, or $C_{2-8}$ heteroaryl, and at least one of $R^2$ and $R^4$ is fluoroalkyl; and (2) W and Y are N, Z is CH, X is C—$R^4$, wherein $R^4$ is hydrogen, $C_{1-8}$ alkyl, $C_{1-8}$ fluoroalkyl, $C_{1-8}$ alkoxy, $C_{5-10}$ aryl, or $C_{2-8}$ heteroaryl, and at least one of $R^2$ and $R^4$ is fluoroalkyl; and wherein $R^2$ is $CF_3$ when A is CH, n is 2, X and Z are N, W is CH and Y is C—$R^4$.

2. The organometallic compound as claimed in claim 1, wherein each $R^1$ is independently hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

3. The organometallic compound as claimed in claim 1, wherein each $R^2$ is independently methyl group, ethyl group, propyl group, isopropyl group, butyl group, tert-butyl group, pentyl group, hexyl group, fluoromethyl group, fluoroethyl group, or fluoropropyl group.

4. The organometallic compound as claimed in claim 1, wherein $R^3$ is methyl group, ethyl group, propyl group, isopropyl group, butyl group, tert-butyl group, pentyl group, or hexyl group.

5. The organometallic compound as claimed in claim 1, wherein $R^4$ is hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

6. The organometallic compound as claimed in claim 1, wherein the organometallic compound is

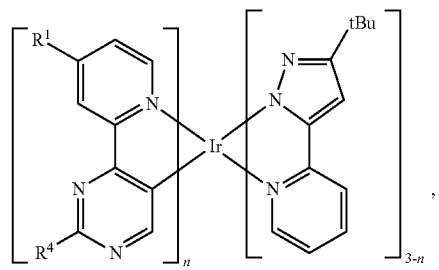

wherein n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^4$ is independently $C_{1-8}$ fluoroalkyl.

7. The organometallic compound as claimed in claim 1, wherein

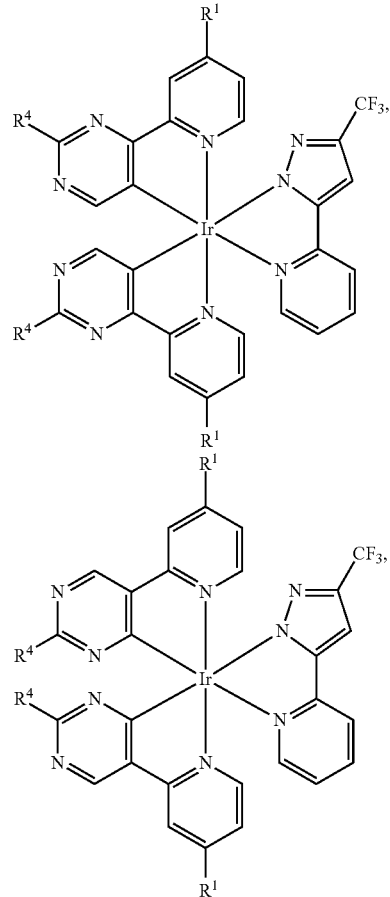

-continued

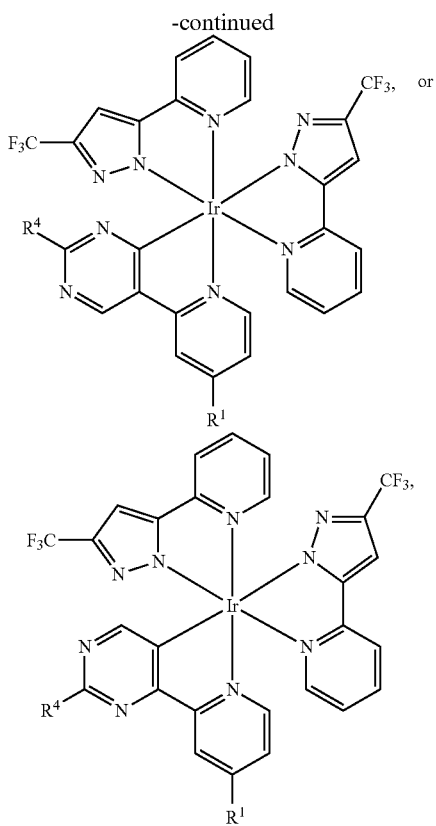

the organometallic compound is
wherein each $R^1$ is independently hydrogen, $C_{1-8}$ alkyl, $C_{1-8}$ alkoxy, $C_{5-10}$ aryl, or $C_{2-8}$ heteroaryl; each $R^4$ is independently hydrogen, $C_{1-8}$ alkyl, $C_{1-8}$ fluoroalkyl, $C_{1-8}$ alkoxy, $C_{5-10}$ aryl, or $C_{2-8}$ heteroaryl; and $R^1$ is not hydrogen when $R^4$ is hydrogen.

8. The organometallic compound as claimed in claim 1, wherein the organometallic compound is

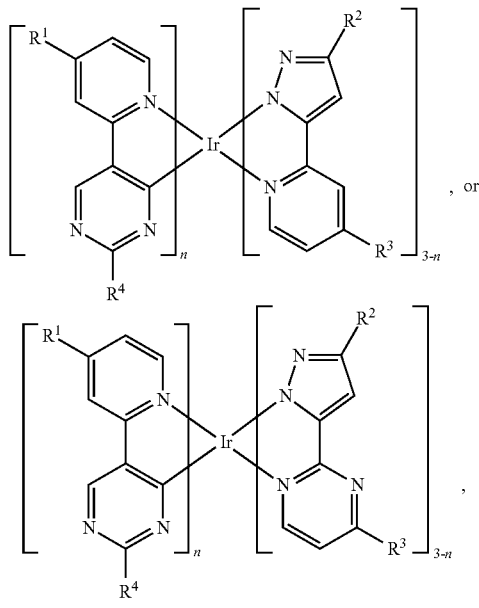

wherein each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; each $R^3$ is independently hydrogen, or $C_{1-8}$ alkyl; and, each $R^4$ is independently hydrogen, $C_{1-8}$ alkyl, $C_{1-8}$ fluoroalkyl, $C_{1-8}$ alkoxy, $C_{5-10}$ aryl, or $C_{2-8}$ heteroaryl, and wherein at least one of $R^2$ and $R^4$ is fluoroalkyl when n is 1; and $R^2$ is $CF_3$ when n is 2.

9. The organometallic compound as claimed in claim 1, wherein the organometallic compound is

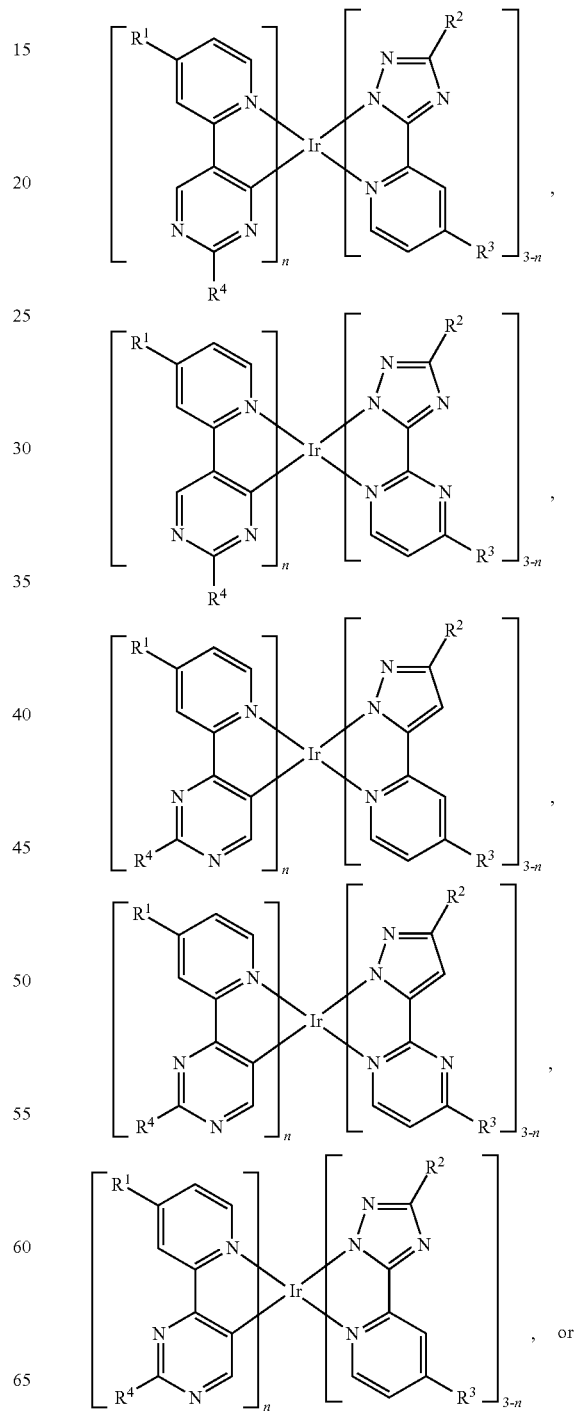

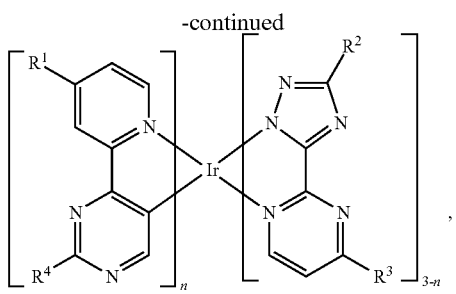

wherein each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; each $R^3$ is independently hydrogen, or $C_{1-8}$ alkyl; and, each $R^4$ is independently hydrogen, $C_{1-8}$ alkyl, $C_{1-8}$ alkoxy, $C_{1-8}$ fluoroalkyl, $C_{5-10}$ aryl, or $C_{2-8}$ heteroaryl, and wherein at least one of $R^2$ and $R^4$ is fluoroalkyl.

10. An organic light-emitting device, comprising:
a pair of electrodes; and
an electroluminescent element, disposed between the pair of electrodes, wherein the electroluminescent element comprises an organometallic compound, wherein the organometallic compound has a Formula (I) or Formula (II), of:

Formula (I)

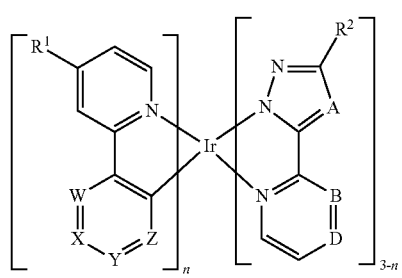

Formula (II)

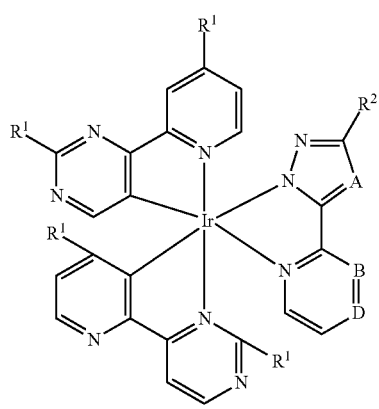

wherein, n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl, or $C_{1-8}$ alkyl; A is N, or CH; B is N, or CH; D is N, or C—$R^3$, wherein $R^3$ is H, or $C_{1-8}$ alkyl; and $R^1$ is not hydrogen when $R^2$ is hydrogen, and wherein one of following two conditions (1) and (2) is met: (1) X and Z are N, W is CH, Y is C—$R^4$, wherein $R^4$ is hydrogen, $C_{1-8}$ alkyl, $C_{1-8}$ fluoroalkyl, $C_{1-8}$ alkoxy, $C_{5-10}$ aryl, or $C_{2-8}$ heteroaryl, and at least one of $R^2$ and $R^4$ is fluoroalkyl; and (2) W and Y are N, Z is CH, X is C—$R^4$, wherein $R^4$ is hydrogen, $C_{1-8}$ alkyl, $C_{1-8}$ fluoroalkyl, $C_{1-8}$ alkoxy, $C_{5-10}$ aryl, or $C_{2-8}$ heteroaryl, and at least one of $R^2$ and $R^4$ is fluoroalkyl; and wherein $R^2$ is $CF_3$ when A is CH, n is 2, X and Z are N, W is CH and Y is C—$R^4$.

11. The organic light-emitting device as claimed in claim 10, wherein each $R^1$ is independently hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

12. The organic light-emitting device as claimed in claim 10, wherein each $R^2$ is independently methyl group, ethyl group, propyl group, isopropyl group, butyl group, tert-butyl group, pentyl group, hexyl group, fluoromethyl group, fluoroethyl group, or fluoropropyl group.

13. The organic light-emitting device as claimed in claim 10, wherein $R^3$ is methyl group, ethyl group, propyl group, isopropyl group, butyl group, tert-butyl group, pentyl group, or hexyl group.

14. The organic light-emitting device as claimed in claim 10, wherein R4 is hydrogen, methyl group, ethyl group, propyl group, isopropyl group, butyl group, tert-butyl group, pentyl group, hexyl group, methoxy group, ethoxy group, propoxy group, isopropoxy group, butoxy group, isobutoxy group, pentyloxy group, hexyloxy group, phenyl group, biphenyl group, pyridyl group, furyl group, carbazole group, naphthyl group, anthryl group, phenanthrenyl group, imidazolyl group, pyrimidinyl group, quinolinyl group, indolyl group, or thiazolyl group.

15. The organic light-emitting device as claimed in claim 10, wherein the organometallic compound is

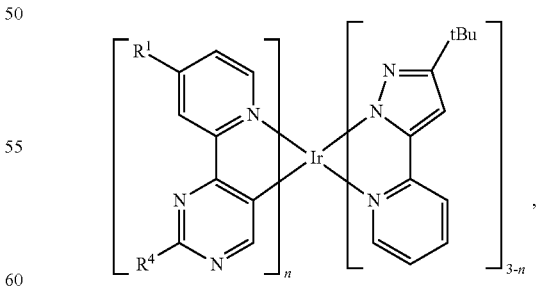

wherein n is 1 or 2; each $R^1$ is independently hydrogen, $C_{1-8}$ alkyl, $C_{1-8}$ alkoxy, $C_{5-10}$ aryl, or $C_{2-8}$ heteroaryl; each $R^4$ is independently $C_{1-8}$ fluoroalkyl.

16. The organic light-emitting device as claimed in claim 10, wherein the organometallic compound is

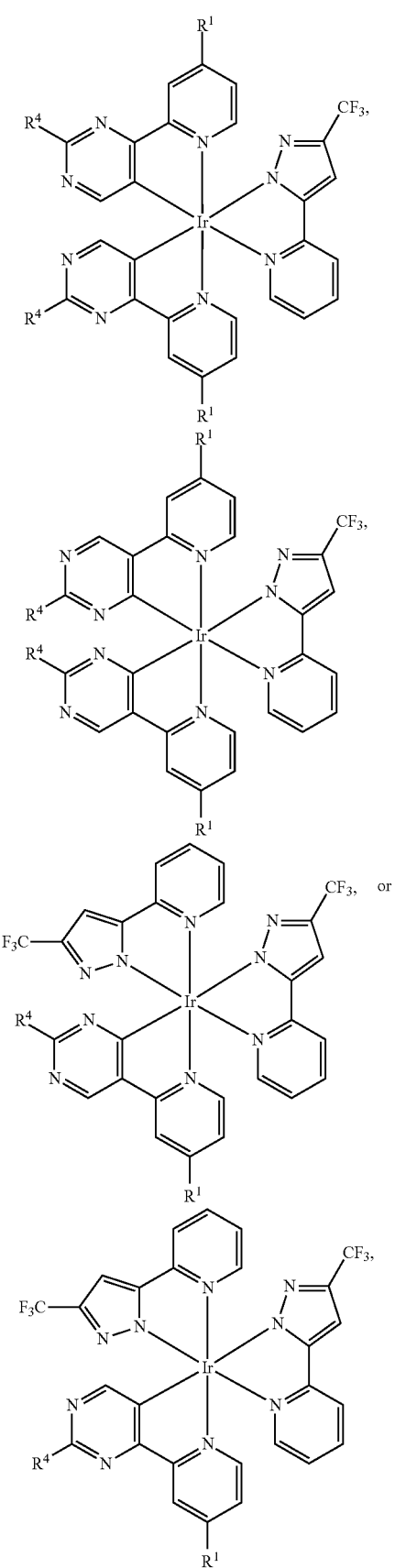

wherein each $R^1$ is independently hydrogen, $C_{1-8}$ alkyl, $C_{1-8}$ alkoxy, $C_{5-10}$ aryl, or $C_{2-8}$ heteroaryl; each $R^4$ is independently hydrogen, $C_{1-8}$ alkyl, $C_{1-8}$ fluoroalkyl, $C_{1-8}$ alkoxy, $C_{5-10}$ aryl, or $C_{2-8}$ heteroaryl; and $R^1$ is not hydrogen when $R^4$ is hydrogen.

17. The organic light-emitting device as claimed in claim 10, wherein the organometallic compound is

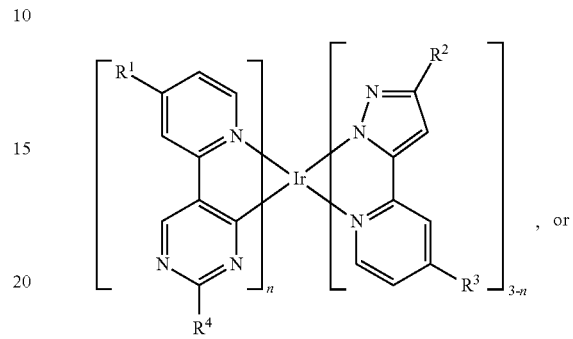

wherein each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; each $R^3$ is independently hydrogen, or $C_{1-8}$ alkyl; and, each $R^4$ is independently hydrogen, $C_{1-8}$ alkyl, $C_{1-8}$ fluoroalkyl, $C_{1-8}$ alkoxy, $C_{5-10}$ aryl, or $C_{2-8}$ heteroaryl, and wherein at least one of $R^2$ and $R^4$ is fluoroalkyl when n is 1; and $R^2$ is $CF_3$ when n is 2.

18. The organic light-emitting device as claimed in claim 10, wherein the organometallic compound is

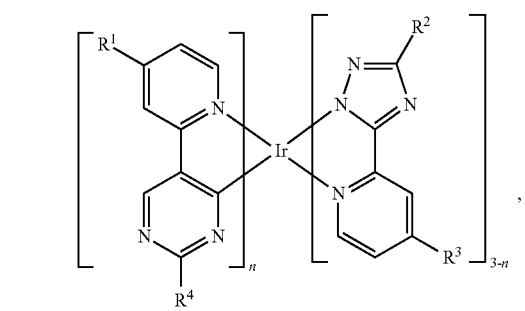

-continued

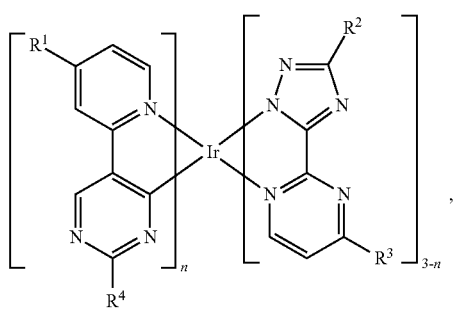

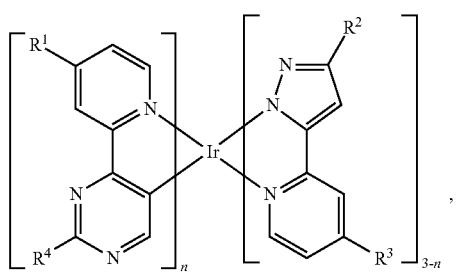

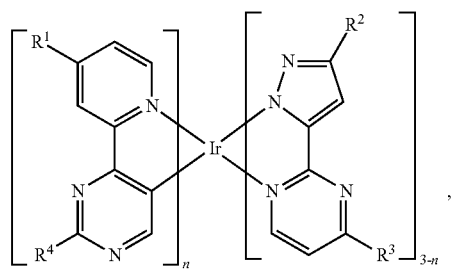

-continued

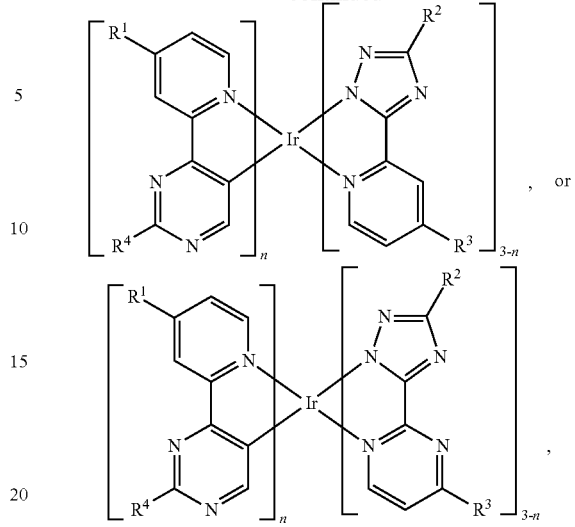

wherein each $R^1$ is independently hydrogen, $C_{1-8}$ alkyl, $C_{1-8}$ alkoxy, $C_{5-10}$ aryl, or $C_{2-8}$ heteroaryl; each $R^2$ is independently hydrogen, $C_{1-8}$ fluoroalkyl group, or $C_{1-8}$ alkyl group; each $R^3$ is independently hydrogen, or $C_{1-8}$ alkyl; and, each $R^4$ is independently hydrogen, $C_{1-8}$ alkyl, $C_{1-8}$ alkoxy, $C_{1-8}$ fluoroalkyl, $C_{5-10}$ aryl, or $C_{2-8}$ heteroaryl, and wherein at least one of $R^2$ and $R^4$ is fluoroalkyl.

19. The organic light-emitting device as claimed in claim 10, wherein the electroluminescent element emits blue or green light under a bias voltage.

20. A lighting device, comprising:
a lead frame; and
the organic light-emitting device as claimed in claim 10, disposed on the lead frame.

* * * * *